United States Patent
Inui et al.

(10) Patent No.: US 10,738,296 B2
(45) Date of Patent: Aug. 11, 2020

(54) TRANSFORMANT FOR PRODUCING 4-HYDROXYBENZOIC ACID OR SALT THEREOF

(71) Applicant: GREEN CHEMICALS CO., LTD., Kyoto (JP)

(72) Inventors: Masayuki Inui, Kyoto (JP); Kazumi Hiraga, Kyoto (JP); Masako Suda, Kyoto (JP); Ryoma Hashimoto, Kyoto (JP)

(73) Assignee: GREEN CHEMICALS CO., LTD., Kyoto (JP)

( * ) Notice: Subject to any disclaimer, the term of this patent is extended or adjusted under 35 U.S.C. 154(b) by 0 days.

(21) Appl. No.: 16/244,809

(22) Filed: Jan. 10, 2019

(65) Prior Publication Data
US 2019/0136222 A1    May 9, 2019

Related U.S. Application Data

(62) Division of application No. 15/309,332, filed as application No. PCT/JP2015/063738 on May 13, 2015, now Pat. No. 10,221,409.

(30) Foreign Application Priority Data

May 14, 2014  (JP) ................. 2014-100875

(51) Int. Cl.
| | | |
|---|---|---|
| *C12N 9/88* | (2006.01) | |
| *C12N 15/09* | (2006.01) | |
| *C12P 7/42* | (2006.01) | |
| *C12N 15/77* | (2006.01) | |

(52) U.S. Cl.
CPC ............... *C12N 9/88* (2013.01); *C12N 15/09* (2013.01); *C12N 15/77* (2013.01); *C12P 7/42* (2013.01); *C12Y 401/0304* (2013.01)

(58) Field of Classification Search
CPC .......... C12N 9/88; C12N 15/77; C12N 15/09; C12Y 401/0304; C12P 7/42
See application file for complete search history.

(56) References Cited

U.S. PATENT DOCUMENTS

| 6,030,819 A | 2/2000 | Amaratunga et al. |
| 6,114,157 A | 9/2000 | Johnson et al. |
| 2013/0273624 A1* | 10/2013 | Yukawa ............ C12N 9/88 435/156 |

FOREIGN PATENT DOCUMENTS

| JP | 2012-183048 | 9/2012 |
| KR | 10-2015-0054237 | 5/2015 |
| WO | 2012/063862 | 5/2012 |

OTHER PUBLICATIONS

Atsumi et al., Appl. Microbiol. Biotechnol. 85:651-657, 2010.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Sadowski et al., Current Opinion in Structural Biology 19:357-362, 2009.*
Barisic et al., GenBank accession No. CDL55597, Jan. 2, 2014.*
McClelland et al., GenBank accession No. ABV14952, Jan. 31, 2014.*
Nam et al., GenBank accession No. AWV28785, Jun. 18, 2018.*
Gualtieri et al., GenBank accession No. CDL81741, Jan. 23, 2014.
Branden et al., Introduction to Protein Structure, Garland Publishing Inc., New York, p. 247, 1991.
International Search Report dated Aug. 11, 2015 in International Application No. PCT/JP2015/063738.
Natasha Smith et al., "Structural analysis of ligand binding and catalysis in chorismate lyase", Arch. Biochem. Biophys., Jan. 1, 2006, 445(1), p. 72-80, Epub Nov. 22, 2005.
Marion Siebert et al., "Formation of 4-hydroxybenzoate in *Escherichia coli*: characterization of the *ubiC* gene and its encoded enzyme chorismate pyruvate-lyase", Microbiology, Apr. 1994, 140(4), p. 897-904.
Travis Gallagher, "Protein packing interactions and polymorphy of chorismate lyase from *E. coli*", Journal of Crystal Growth, Nov. 2001, 232(1-4), p. 215-20.
Brian P. Nichols, et al., "Cloning and Sequencing of *Escherichia coli ubiC* and Purification of Chorismate Lyase", J. Bacteriol., 1992, vol. 174, No. 16, p. 5309-5316.
R. Muller et al., "Microbial production of specifically ring-$^{13}$C-labelled 4-hydroxybenzoic acid", Appl. Microbiol. Biotechnol., 1995, vol. 43, p. 985-988.
Jessica L. Barker et al., "Microbial Synthesis of p-Hydrozybenzoic Acid from Glucose", Biotechnol. Bioeng., 2001, vol. 76, p. 376-390.
M.J. Holden et al., "Chorismate lyase: kinetics and engineering for stability", Biochimica et Biophysica Acta, 2002, 1594, p. 160-167.

(Continued)

*Primary Examiner* — Delia M Ramirez
(74) *Attorney, Agent, or Firm* — Wenderoth, Lind & Ponack, L.L.P.

(57) ABSTRACT

The mutant chorismate-pyruvate lyase (A) or (B) as described below is capable of producing 4-hydroxybenzoic acid or a salt thereof with sufficient practical efficiency.

(A) A mutant chorismate-pyruvate lyase obtained by replacing the valine at position 80 in a chorismate-pyruvate lyase (ubiC) from *Pantoea ananatis* consisting of the amino acid sequence of SEQ ID NO: 1 with one or more other amino acids.

(B) A mutant chorismate-pyruvate lyase obtained by replacing an amino acid in another chorismate-pyruvate lyase, the amino acid being at a position enzymologically homologous with that of the above valine, with one or mere other amino acids.

7 Claims, 1 Drawing Sheet

Specification includes a Sequence Listing.

(56) References Cited

OTHER PUBLICATIONS

International Preliminary Report on Patentability dated Nov. 15, 2016 in corresponding International Application No. PCT/JP2015/063738.
Extended European Search Report dated Sep. 7, 2017 in corresponding European patent application No. 15793452.2.
Database UniProt, Sep. 22, 2009, accession No. C7BNG4.
Database UniProt, Oct. 3, 2012, accession No. J3BQV8.
Wilkinson et al., GenBank accession No. CAQ86019; Jul. 24, 2009.

* cited by examiner

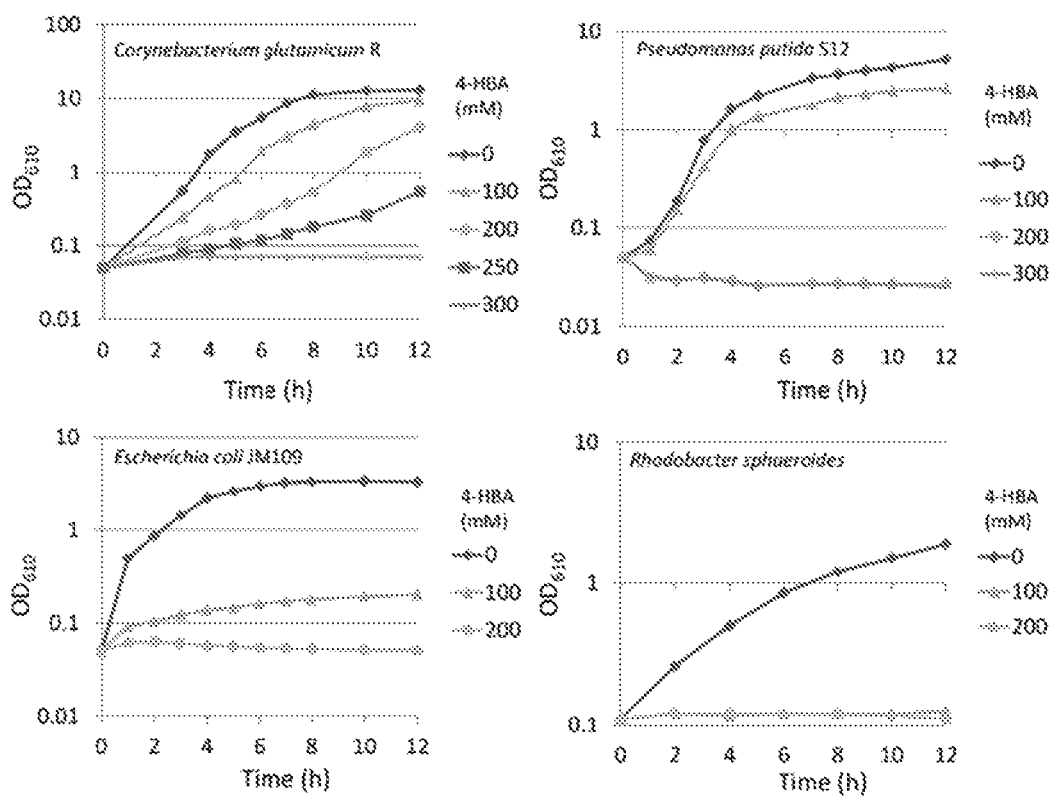

TRANSFORMANT FOR PRODUCING 4-HYDROXYBENZOIC ACID OR SALT THEREOF

TECHNICAL FIELD

The present invention provides a mutant enzyme modified for improved productivity to produce 4-hydroxybenzoic acid or a salt thereof (hereinafter may be abbreviated as "4-HBA"), a coryneform bacterium transformant having an improved 4-HBA productivity as a result of higher expression of the mutant enzyme, and an efficient 4-HBA-producing process using the transformant.

BACKGROUND ART

Against the backdrop of global warming and exhaustion of fossil resources, production of chemical products using renewable resources has attracted attention as an emerging industry for realizing a low-carbon society.

4-HBA is a useful substance used as a raw material for liquid-crystal polymers, as a raw material for the synthesis of paraben, which is an antimicrobial agent, and the like.

Currently, 4-HBA is produced by chemical conversion from crude oil as a raw material. Examples of chemical 4-HBA production processes include a process in which phenol, potassium hydroxide, and carbon dioxide are reacted under high-pressure conditions.

Such a process depends on fossil materials for phenol as the starting material, and in addition, places a great burden on the environment because the process requires strong alkali, carbon dioxide, and high-temperature and high-pressure conditions, and produces hazardous liquid waste.

Therefore, there is a strong need to establish an energy-saving, environment-conscious process that allows biological production of 4-HBA and produces a reduced amount of hazardous liquid waste.

However, biological production of 4-HBA from renewable resources is less productive as compared to production of lactic acid or ethanol because the metabolic reaction from a raw material sugar consists of a great many steps. In addition, there are problems, such as inhibition of bacterial growth by produced 4-HBA and cytotoxicity of 4-HBA. Therefore, industrial production of 4-HBA has not been achieved.

Using *Escherichia coli*, it has been revealed that 4-HBA is synthesized from chorismic acid, which is an intermediate in the shikimate pathway involved in the synthesis of aromatic amino acids etc., by chorismate-pyruvate lyase encoded by ubiC (Non Patent Literature 1 and 2, Patent Literature 1 and 2).

There is a report of introduction of a chorismate pyruvate-lyase gene (ubiC) of *Escherichia coli* into a different kind of microorganism, *Klebsiella pneumoniae*, as a host, in an attempt to produce 4-HBA (Non Patent Literature 3). Also, there is a report of fermentative production of 4-HBA in an *Escherichia coli* in which the shikimic acid pathway is reinforced (Non Patent Literature 4). In an attempt to avoid the growth inhibition or the toxic action by 4-HBA, there are reports of selection of 4-HBA-resistant strains and of culture in the presence of an ion-exchange resin, but practically sufficient 4-HBA productivity has not been achieved (Non Patent Literature 2).

Regarding ubiCs of other living organisms than *Escherichia coli*, the ubiC of *Rhodobacter sphaeroides* has been reported. However, an *Escherichia coli* transformant highly expressing ubiC and a *Rhodobacter sphaeroides* transformant highly expressing ubiC are capable of producing 4-HBA only at low concentrations, which are not practically sufficient (Patent Literature 3). Also, despite the description that the ubiC of *Rhodobacter sphaeroides* can complement the ubiC of *Escherichia coli* in a disruptant of *Escherichia coli* lacking the ubiC gene, the literature does not include any enzymatic activity values, description regarding enzymatic characteristics, or detailed description regarding comparison with enzymes from other living organisms.

The UbiC of *Escherichia coli* has already been enzymatically analyzed in detail, and is known to be strongly inhibited by the product, 4-HBA (product inhibition) (Non Patent Literature 2 and 5). Therefore, in order to establish a high 4-HBA-producing strain aiming at a higher production of 4-HBA, obtaining a highly active ubiC and obtaining a resistant ubiC against product inhibition by 4-HBA are extremely important.

CITATION LIST

Non Patent Literature

Non Patent literature 1: J. Bacteriol., 174, 5309-5316 (1992)
Non Patent literature 2: Microbiology, 140, 897-904 (1994)
Non Patent literature 3: Appl. Microbiol. Biotechnol., 43, 985-988 (1995)
Non Patent literature 4: Biotechnol. Bioeng., 76, 376-390 (2001)
Non Patent Literature 5: Biochimica et Biophysica Acta, 1594, 160-167 (2002)

Patent Literature

Patent literature 1: U.S. Pat. No. 6,030,819
Patent literature 2: U.S. Pat. No. 6,114,157
Patent literature 3: JP 2012-183048 A

SUMMARY OF INVENTION

Technical Problem

An object of the present invention is to provide a mutant chorismate-pyruvate lyase having a practically sufficient level of 4-HBA-producing activity; a transformant which highly expresses the enzyme and thereby is capable of efficiently producing 4-HBA; and a process for efficiently producing 4-HBA using the transformant.

Solution to Problem

The present inventors have wholeheartedly carried out investigations in order to achieve the object described above and found that a mutant chorismate-pyruvate lyase having an improved ability to produce 4-HBA from glucose, chorismic acid, or the like can be obtained by introducing a mutation to a ubiC gene, which mutation being replacement of (A) valine at position 80 in a chorismate-pyruvate lyase (ubiC) from *Pantoea ananatis* consisting of the amino acid sequence of SEQ ID NO: 1, or (B) an amino acid in another chorismate-pyruvate lyase, the amino acid being at a position enzymologically homologous with that of the above valine, with a different amino acid.

The present invention, which has been completed based on the above-mentioned findings, provides the following mutant chorismate-pyruvate lyases, transformants and processes for producing 4-HBA.

[1] A mutant chorismate-pyruvate lyase of the following (A) or (B).

(A) A mutant chorismate-pyruvate lyase obtained by replacing valine at position 80 in a chorismate-pyruvate lyase (ubiC) from *Pantoea ananatis* consisting of the amino acid sequence of SEQ ID NO: 1 with one or more other amino acids.

(B) A mutant chorismate-pyruvate lyase obtained by replacing an amino acid in another chorismate-pyruvate lyase, the amino acid being at a position enzymologically homologous with that of the above valine, with one or more other amino acids.

[2] The mutant chorismate-pyruvate lyase of the above [1], wherein the mutant chorismate-pyruvate lyase (B) is obtained by replacing (i) valine (V) at position 80 in a chorismate-pyruvate lyase from a *Providencia* bacterium, (ii) isoleucine (I) at position 79 in a chorismate-pyruvate lyase from an *Escherichia* bacterium, or (iii) isoleucine (I) at position 79 in a chorismate-pyruvate lyase from a *Cronobacter* bacterium with one or more other amino acids.

[3] The mutant chorismate-pyruvate lyase of the above [1], which is the following (a), (b), or (c):

(a) a mutant chorismate-pyruvate lyase obtained by replacing valine at position 80 in a chorismate-pyruvate lyase from *Pantoea ananatis* consisting of the amino acid sequence of SEQ ID NO: 1, valine at position 80 in a chorismate-pyruvate lyase from *Providencia stuartii* consisting of the amino acid sequence of SEQ ID NO: 2, valine at position 80 in a chorismate-pyruvate lyase from *Providencia rustigianii* consisting of the amino acid sequence of SEQ ID NO: 3, valine at position 80 in a chorismate-pyruvate lyase from *Providencia sneebia* consisting of the amino acid sequence of SEQ ID NO: 4, valine at position 80 in a chorismate-pyruvate lyase from *Providencia rettgeri* consisting of the amino acid sequence of SEQ ID NO: 5, valine at position 80 in a chorismate-pyruvate lyase from *Providencia alcalifaciens* consisting of the amino acid sequence of SEQ ID NO: 6, or valine at position 80 in a chorismate-pyruvate lyase from *Providencia burhodogranariea* consisting of the amino acid sequence of SEQ ID NO: 7, isoleucine at position 79 in a chorismate-pyruvate lyase from *Escherichia coli* consisting of the amino acid sequence of SEQ ID NO: 8, or isoleucine at position 79 in a chorismate-pyruvate lyase from *Cronobacter sakazakii* consisting of the amino acid sequence of SEQ ID NO: 9 with one or more other amino acids;

(b) a mutant chorismate-pyruvate lyase, which consists of an amino acid sequence having the amino-acid segment introduced by the above replacement and having 90% or more of identity with any one of SEQ ID NOs: 1 to 9, and has chorismate-pyruvate lyase activity; or (c) a mutant chorismate-pyruvate lyase as a polypeptide which consists of an amino acid sequence having 90% or more of identity with any one of SEQ ID NOs: 1 to 9, has chorismate-pyruvate lyase activity, and has a replacement of an amino acid at a position enzymologically homologous with that of valine at position 80 of any one of SEQ ID NOs: 1 to 7 or isoleucine at position 79 of SEQ ID NO: 8 or 9 with one or more other amino acids.

[4] The mutant chorismate-pyruvate lyase of any one of the above [1] to [3], wherein the valine or isoleucine is replaced with one amino acid which is alanine, cysteine, threonine, serine, or asparagine.

[5] A transformant obtained by introducing, into a coryneform bacterium as a host, a DMA which encodes the mutant chorismate-pyruvate lyase of any one of the above [1] to [4].

[6] The transformant of the above [5], wherein the coryneform bacterium as the host is a *Corynebacterium*.

[7] The transformant of the above [6], wherein the *Corynebacterium glutamicum* is *Corynebacterium glutamicum* R (FERM BP-18976), ATCC13032, or ATCC13869.

[8] A transformant obtained by introducing the following mutant DMA:

(C) a mutant DNA obtained by replacing gtc at positions 240 to 242 in a chorismate-pyruvate lyase (ubiC) gene of *Pantoea ananatis* consisting of the base sequence of SEQ ID NO: 10 with a DNA segment which encodes one or more amino acids different from the amino acid encoded by gtc; or (D) a mutant DNA obtained by replacing a DNA segment in a gene which encodes another chorismate-pyruvate lyase, the DNA segment being at positions corresponding to the above gtc, with a DNA segment which encodes one or more amino acids different from the amino acid encoded by the original DNA segment into a coryneform bacterium as a host.

[9] The transformant of the above [8], wherein the DNA of the above (D) is a mutant DNA obtained by replacing (iv) gtc at positions 240 to 242 in a chorismate-pyruvate lyase gene of a *Providencia* bacterium, (v) atc at positions 237 to 239 in a chorismate-pyruvate lyase gene of an *Escherichia* bacterium, or (vi) atc at positions 237 to 239 in a chorismate-pyruvate lyase gene of a *Cronobacter* bacterium with a DNA segment which encodes one or more amino acids different from the amino acid encoded by the original DNA segment.

[10] The transformant of the above [8], wherein the mutant DNA is the following (d), (e), or (f).

(d) A mutant DNA obtained by replacing gtc at positions 240 to 242 in a chorismate-pyruvate lyase gene of *Pantoea ananatis* consisting of the base sequence of SEQ ID NO: 10, a chorismate-pyruvate lyase gene of *Providencia stuartii* consisting of the base sequence of SEQ ID NO: 11, a chorismate-pyruvate lyase gene of *Providencia rustigianii* consisting of the base sequence of SEQ ID NO: 12, a chorismate-pyruvate lyase gene of *Providencia sneebia* consisting of the base sequence of SEQ ID NO: 13, a chorismate-pyruvate lyase gene of *Providencia rettgeri* consisting of the base sequence of SEQ ID NO: 14, a chorismate-pyruvate lyase gene of *Providencia alcalifaciens* consisting of the base sequence of SEQ ID NO: 15, or a chorismate-pyruvate lyase gene of *Providencia burhodogranariea* consisting of the base sequence, of SEQ ID NO: 16 with a DNA segment which encodes one or more amino acids different from valine, a mutant DNA obtained by replacing atc at positions 237 to 239 in a chorismate-pyruvate lyase gene of *Escherichia coli* consisting of the base sequence of SEQ ID NO: 17 with a DNA segment which encodes one or more amino acids different from isoleucine, or a mutant DNA obtained by replacing atc at positions 237 to 239 in a chorismate-pyruvate lyase gene of *Cronobacter sakazakii* consisting of the base sequence of SEQ ID NO: 18 with a DNA segment which encodes one or more amino acids different from isoleucine.

(e) A mutant DNA, which consists of a base sequence having the DNA segment introduced by the above replacement and having 90% or more of identity with any one of SEQ ID NOs: 10 to 18, and encodes a polypeptide having chorismate-pyruvate lyase activity.

(f) A mutant DNA which consists of a base sequence having 90% or more of identity with any one of SEQ ID NOs: 10 to 18; encodes a polypeptide having chorismate-pyruvate lyase activity; and has a replacement of gtc at positions 240 to 242 in any one of SEQ ID NOs: 10 to 16 with a DNA segment which encodes one or more amino acids different from valine, or a replacement of a DNA segment; corresponding to atc at positions 237 to 239 in SEQ ID NO: 17 or 18 with a DNA segment which encodes one or more amino acids different from isoleucine
(here, the DNA segment at positions 240 to 242 in any one of SEQ ID NOs: 10 to 16 corresponding to gtc is a DNA which encodes an amino acid at a position enzymologically homologous with that of valine at position 80 of a chorismate-pyruvate lyase encoded by a DNA consisting of the base sequence of any one of SEQ ID NOs: 10 to 16; and the DNA segment corresponding to gtc at positions 237 to 239 in SEQ ID NO: 17 or 18 is a DNA which encodes an amino acid at a position enzymologically homologous with that of isoleucine at position 79 of a chorismate-pyruvate lyase encoded by a DNA consisting of the base sequence of SEQ ID NO: 17 or 18).

[11] The transformant of any one of the above [8] to [10], wherein the DNA introduced by the above replacement is gca, tgc, acc, tcc, or aac.

[12] The transformant of any one of the above [8] to [11], wherein the coryneform bacterium as the host is a *Corynebacterium*.

[13] The transformant of the above [12], wherein the *Corynebacterium glutamicum* is *Corynebacterium glutamicum* R (FERM BP-18976), ATCC13032, or ATCC13869.

[14] *Corynebacterium glutamicum* HBA-47 (Accession Number: NITE BP-01849), which is a transformant of *Corynebacterium glutamicum*.

[15] A process for producing 4-hydroxybenzoic acid or a salt thereof, which comprises a step of culturing the transformant of any one of the above [5] to [14] in a reaction mixture containing at least one starting compound selected from the group consisting of a sugar, a compound that can be metabolized into chorismic acid by the transformant, chorismic acid, and a salt thereof, and a step of recovering 4-hydroxybenzoic acid or a salt thereof from the reaction mixture.

[16] The process of the above [15], wherein the transformant is cultured under aerobic conditions where the transformant does not grow.

Advantageous Effects of Invention

Using the mutant chorismate-pyruvate lyase of the present invention, or a coryneform bacterium transformant obtained by introducing a DNA which encodes the mutant chorismate-pyruvate lyase gene, 4-HBA can be produced with sufficient practical efficiency from a sugar, a compound that can be metabolized into chorismic acid by the transformant, chorismic acid, and a salt thereof.

BRIEF DESCRIPTION OF DRAWING

FIG. 1 shows the effect of 4-hydroxybenzoic acid on the growth of four kinds of microorganisms (*Corynebacterium glutamicum* R, *Escherichia coli* JM109, *Pseudomonas putida* S12 ATCC700801, and *Rhodobacter sphaeroides* NBRC12203).

DESCRIPTION OF EMBODIMENTS

Hereinafter, the present invention will be described in detail.

(1) Mutant Chorismate-Pyruvate Lyase

The mutant chorismate-pyruvate lyase of the present invention is (A) a mutant chorismate-pyruvate lyase obtained by replacing valine at position 80 in a chorismate-pyruvate lyase (ubiC) from *Pantoea ananatis* consisting of the amino acid sequence of SEQ ID NO: 1 with another amino acid(s), or (B) a mutant chorismate-pyruvate lyase obtained by replacing an amino acid in another chorismate-pyruvate lyase, the amino acid being at a position enzymologically homologous with that of the above valine, with another amine acid(s).

Examples of the above mutant chorismate-pyruvate lyase (B) include a mutant chorismate-pyruvate lyase obtained by replacing (i) valine (V) at position 80 in a chorismate-pyruvate lyase from a *Providencia* bacterium, (ii) isoleucine (I) at position 79 in a chorismate-pyruvate lyase from an *Escherichia* bacterium, or (iii) isoleucine (I) at position 79 in a chorismate-pyruvate lyase from a *Cronobacter* bacterium with another amino acid(s).

Examples of the chorismate-pyruvate lyase from a *Providencia* bacterium include a chorismate-pyruvate lyase from *Providencia stuartii* consisting of the amino acid sequence of SEQ ID NO: 2, a chorismate-pyruvate lyase from *Providencia rustigianii* consisting of the amino acid sequence of SEQ ID NO: 3, a chorismate-pyruvate lyase from *Providencia sneebia* consisting of the amino acid sequence of SEQ ID NO: 4, a chorismate-pyruvate lyase from *Providencia rettgeri* consisting of the amino acid sequence of SEQ ID NO: 5, a chorismate-pyruvate lyase from *Providencia alcalifaciens* consisting of the amino acid sequence of SEQ ID NO: 6, and a chorismate-pyruvate lyase from *Providencia burhodogranariea* consisting of the amino acid sequence of SEQ ID NO: 7.

Examples of the chorismate-pyruvate lyase from an *Escherichia* bacterium include a chorismate-pyruvate lyase from *Escherichia coli* consisting of the amino acid sequence of SEQ ID NO: 8.

Examples of the chorismate-pyruvate lyase from a *Cronobacter* bacterium include a chorismate-pyruvate lyase from *Cronobacter sakazakii* consisting of the amino acid sequence of SEQ ID NO: 9.

The above-mentioned valine or isoleucine may be replaced with another amino acid or two or more (for example, 2 to 8, 2 to 6, 2 to 3, or 2) amino acids. Preferably, the valine or isoleucine is replaced with one amino acid. In particular, the valine or isoleucine is preferably replaced with alanine (A), cysteine (C), threonine (T), serine (S), or asparagine (N), and more preferably replaced with alanine (A) or cysteine (C).

Instead of the replacement of the valine or isoleucine, deletion of the valine or isoleucine, deletion of one or more (for example, 2 to 8, 2 to 6, 2 to 3, or 2) amino acids adjacent to the N-terminal side of the valine or isoleucine, or insertion of one or more (for example, 2 to 8, 2 to 6, 2 to 3, or 2) amino acids to the position adjacent to the valine or isoleucine can also be employed to enhance the chorismate-pyruvate lyase activity.

The mutant chorismate-pyruvate lyase of the present invention includes a mutant chorismate-pyruvate lyase which consists of a polypeptide having the amino-acid segment introduced by the mutation (for example, alanine, cysteine, threonine, serine, or asparagine) and having 90% or more, preferably 95% or more, more preferably 98% or more of identity with any one of SEQ ID NOs: 1 to 9, and has chorismate-pyruvate lyase activity. That is, in the mutant chorismate-pyruvate lyase, the amino acid at a position enzymologically homologous with that of the valine at position 80 of any one of SEQ ID NOs: 1 to 7 or the isoleucine at position 75 of SEQ ID NO: 8 or 9 is not valine or isoleucine but alanine, cysteine, threonine, serine, or asparagine, for example.

In the present invention, "enzymologically homologous" means being equivalent in contribution to the enzymatic function of the polypeptide. The amino acid located at an equivalent position in an amino-acid alignment will equivalently contribute to the enzymatic function.

In the present invention, the homologies of amino acid sequences and the homologies of base sequences were calculated using GENETYX Ver. 8 (made by Genetyx).

Chorismate-pyruvate lyase is an enzyme that catalyzes a reaction in which 4-HBA is produced by elimination of pyruvic acid from chorismic acid and the reverse reaction thereof.

The chorismate-pyruvate lyase activity can be measured by an altered method of the method described in "Microbiology, 140, 897-904 (1994)". Briefly, the enzyme to be tested is added to a test solution containing 50 mM of Tris-HCl (pH 7.5), 0.5 mM of chorismate Ba salt, 0.2 mM of NADH, 0.2 M of NaCl and 5 units of lactate dehydrogenase, the reaction is allowed to proceed at 33° C., and the decrease in absorbance of NADH at 340 nm is monitored to determine the initial rate of the reaction. Using a system not containing the chorismate Ba salt, the reaction is performed in a similar manner to obtain background values. The difference between the measurements is considered to result from the chorismate-pyruvate lyase activity. When linear reduction in the absorbance of NADH at 340 nm with time is observed (which reduction depends on the enzyme and the substrate added), chorismate-pyruvate lyase activity is judged to exist. One unit of enzyme activity is defined as the amount of the enzyme that produces 1 μmol of 4-HBA per minute, and is calculated from the initial rate of the enzyme reaction.

The mutant chorismate-pyruvate lyase of the present invention includes a mutant chorismate-pyruvate lyase as a polypeptide which has 90% or more, preferably 95% or more, more preferably 98% or more of identity with any one of SEQ ID NOs: 1 to 9, has chorismate-pyruvate lyase activity, and has a replacement of an amino acid at a position enzymologically homologous with that of valine at position 30 of any one of SEQ ID NOs: 1 to 7 or isoleucine at position 79 of SEQ ID NO: 8 or 9 with one or more other amino acids (for example, alanine, cysteine, threonine, serine, or asparagine; in particular, alanine or cysteine).

(2) *Corynebacterium* transformant

By introducing a mutant DNA which encodes the above-described mutant chorismate-pyruvate lyase into a coryneform bacterium as a host, a transformant capable of efficiently producing 4-HBA can be obtained.

Examples of the mutant DNA include a mutant DNA obtained by replacing (C) gtc at positions 240 to 242 in a chorismate-pyruvate lyase (ubiC) gene of *Pantoea ananatis* consisting of the base sequence of SEQ ID NO: 10; or (D) a DNA segment at positions corresponding to the above gtc in a gene which encodes another chorismate-pyruvate lyase with a DNA segment which encodes one or more (for example, 2 to 8, 2 to 6, 2 to 3, or 2) amino acids different from the amino acid encoded by the original DNA segment.

Examples of the mutant DNA of the above (D) include a mutant DNA obtained by replacing (iv) gtc at positions 240 to 242 in a chorismate-pyruvate lyase gene of a *Providencia* bacterium, (v) atc at positions 237 to 239 in a chorismate-pyruvate lyase gene of an *Escherichia* bacterium, or (vi) atc at positions 237 to 239 in a chorismate-pyruvate lyase gene of a *Cronobacter* bacterium with a DNA segment which encodes one or more (for example, 2 to 8, 2 to 6, 2 to 3, or 2) different amino acids.

Examples of the chorismate-pyruvate lyase gene of a *Providencia bacterium* include a chorismate-pyruvate lyase gene of *Providencia stuartii* consisting of the base sequence of SEQ ID NO: 11, a chorismate-pyruvate lyase gene of *Providencia rustigianii* consisting of the base sequence of SEQ ID NO: 12, a chorismate-pyruvate lyase gene of *Providencia sneebia* consisting of the base sequence of SEQ ID NO: 13, a chorismate-pyruvate lyase gene of *Providencia rettgeri* consisting of the base sequence of SEQ ID NO: 14, a chorismate-pyruvate lyase gene of *Providencia alcalifaciens* consisting of the base sequence of SEQ ID NO: 15, and a chorismate-pyruvate lyase gene of *Providencia burhodogranariea* consisting of the base sequence of SEQ ID NO: 16.

Examples of the chorismate-pyruvate lyase gene of an *Escherichia bacterium* include a chorismate-pyruvate lyase gene of *Escherichia coli* consisting of the base sequence of SEQ ID NO: 17.

Examples of the chorismate-pyruvate lyase gene of a *Cronobacter bacterium* include a chorismate-pyruvate lyase gene of *Cronobacter sakazakii* consisting of the base sequence of SEQ ID NO: 18.

It is particularly preferable that the DNA segment is replaced with a DNA which encodes one amino acid. In particular, the DNA segment is preferably replaced with a DNA which encodes alanine, cysteine, threonine, serine, or asparagine, and more preferably replaced with a DNA which encodes alanine or cysteine.

Examples of the DNA which encodes alanine include gca, examples of the DNA which encodes cysteine include tgc, examples of the DNA which encodes threonine include acc, examples of the DNA which encodes serine include tcc, and examples of the DNA which encodes cysteine include aac.

The mutant DNA also includes a mutant DNA which consists of a base sequence having the DNA segment introduced by the replacement which segment encodes an amino acid that is not valine or isoleucine (for example, alanine, cysteine, threonine, serine, or asparagine; in particular, alanine or cysteine) and having 90% or more, preferably 95% or more, more preferably 98% or more of identity with any one of SEQ ID NOs: 10 to 18, and encodes a polypeptide having chorismate-pyruvate lyase activity.

The mutant DNA also includes a mutant DNA which has the DNA segment introduced by the replacement which segment encodes an amino acid that is not valine or isoleucine (for example, alanine, cysteine, threonine, serine, or asparagine; in particular, alanine or cysteine), hybridizes to a DNA consisting of any one of SEQ ID NOs: 10 to 18 under stringent, conditions, and encodes a polypeptide having chorismate-pyruvate lyase activity.

In the present invention, "stringent conditions" means conditions in which hybridization is performed in a hybridization solution at a salt concentration of 6×SBC at 50 to 60° C. for 16 hours and then washing with a solution at 0.1× SSC is performed.

The mutant DNA also includes a mutant DNA which consists of a base sequence having 90% or more, preferably 95% or more, more preferably 98% or more of identity with any one of SEQ ID NOs: 10 to 16; encodes a polypeptide having chorismate-pyruvate lyase activity; and has a replacement of a DNA segment corresponding to gtc at positions 240 to 242 in any one of SEQ ID NOs: 10 to 16 with a DNA segment which encodes one or more (for example, 2 to 8, 2 to 6, 2 to 3, or 2) amino acids, in particular, one amino acid different from valine (for example, alanine, cysteine, threonine, serine, or asparagine; in particular, alanine or cysteine).

"The DNA segment corresponding to gtc at positions 240 to 242 in any one of SEQ ID NOs: 10 to 16" means a DNA segment which encodes an amino acid at a position enzymologically homologous with that of valine at position 80 of chorismate-pyruvate lyase consisting of an amino acid sequence encoded by a DNA consisting of the base sequence of any one of SEQ ID NOs: 10 to 16.

The mutant DNA also includes a mutant DNA which consists of a base sequence having 90% or more, preferably 95% or more, more preferably 98% or more of identity with SEQ ID NO: 17 or 18; encodes a polypeptide having chorismate-pyruvate lyase activity; and has a replacement of a DNA segment corresponding to atc at positions 237 to 239 in SEQ ID NO: 17 or 18 with a DNA segment which encodes one or more (for example, 2 to 8, 2 to 6, 2 to 3, or 2) amino acids, in particular, one amino acid different from isoleucine (for example, alanine, cysteine, threonine, serine, or asparagine; in particular, alanine or cysteine).

"The DNA segment corresponding to atc at positions 237 to 239 in SEQ ID NO: 17 or 18" means a DNA segment which encodes an amino acid at a position enzymologically homologous with that of the isoleucine at position 75 of chorismate-pyruvate lyase encoded by a DNA consisting of the base sequence of SEQ ID NO: 17 or 18).

The mutant DNA also includes a mutant DNA which hybridizes to any one of SEQ ID NOs: 10 to 16 under stringent conditions; encodes a polypeptide having chorismate-pyruvate lyase activity; and has a replacement of a DNA segment corresponding to gtc at positions 240 to 242 in any one of SEQ ID NOs: 10 to 16 with a DNA segment which encodes one or more (for example, 2 to 8, 2 to 6, 2 to 3, or 2) amino acids, in particular, one amino acid different from valine (for example, alanine, cysteine, threonine, serine, or asparagine; in particular, alanine or cysteine).

The mutant DNA also includes a mutant. DNA which hybridizes to SEQ ID NO: 17 or 18 under stringent conditions; encodes a polypeptide having chorismate-pyruvate lyase activity; and has a replacement of a DNA segment corresponding to atc at positions 237 to 239 in SEQ ID NO: 17 or 18 with a DNA segment which encodes one or more (for example, 2 to 8, 2 to 6, 2 to 3, or 2) amino acids, in particular, one amino acid different from isoleucine (for example, alanine, cysteine, threonine, serine, or asparagine; in particular, alanine or cysteine).

A DNA analog which has 90% or more of identity with a DNA that encodes chorismate-pyruvate lyase or hybridizes thereto under stringent conditions, and encodes a polypeptide having chorismate-pyruvate lyase activity can be selected from, for example, a DNA library of a different species by PCR or hybridization using a primer or a probe designed based on the base sequence of the original DNA, according to a conventional method, and as a result, a DNA which encodes a polypeptide having chorismate-pyruvate lyase activity can be obtained with a high probability.

The coryneform bacteria are a group of microorganisms defined in Bergey's Manual of Determinative Bacteriology, Vol. 8, 599 (1974), and are not particularly limited as long as they grow under normal aerobic conditions.

The specific examples include the genus *Corynebacterium*, the genus *Brevibacterium*, the genus *Arthrobacter*, the genus *Mycobacterium* and the genus *Micrococcus*. Among the coryneform bacteria, the genus *Corynebacterium* is preferred.

Examples of the genus *Corynebacterium* include *Corynebacterium glutamicum*, *Corynebacterium efficiens*, *Corynebacterium ammoniagenes*, *Corynebacterium halotolerance*, and *Corynebacterium alkanolyticum*. Among them, *Corynebacterium glutamicum* is preferred for safety and high 4-HBA production. Examples of preferred strains include *Corynebacterium glutamicum* R (FERM BP-18976), ATCC13032, ATCC13869, ATCC13058, ATCC13059, ATCC13060, ATCC13232, ATCC13286, ATCC13287, ATCC13655, ATCC13745, ATCC13746, ATCC13761, ATCC14020, ATCC31831, MJ-233 (FERM BP-1497), and MJ-233AB-41 (FERM BP-1498). These strains are deposited internationally under the Budapest Treaty and available to the public.

Among them, strains R (FERM BP-18976), ATCC13032, and ATCC13869 are preferred.

According to molecular biological classification, names of some species of coryneform bacteria, such as *Brevibacterium flavum*, *Brevibacterium lactofermentum*, *Brevibacterium divaricatum*, and *Corynebacterium lilium* are standardized to *Corynebacterium glutamicum* (Liebl, W, et al., Transfer of *Brevibacterium divaricatum* DSM 20297T, "*Brevibacterium flavum*" DSM 20411, "*Brevibacterium lactofermentum*" DSM 20412 and DSM 1412, and *Corynebacterium glutamicum* and their distinction by rRNA gene restriction patterns. Int. J. Syst. Bacteriol. 41:255-260. (1991); and Kazuo Komagata et al., "Classification of the coryneform group of bacteria", Fermentation and Industry, 45:944-963 (1987)).

Examples of the genus *Brevibacterium* include *Brevibacterium armoniagenes* (for example, ATCC6872). The strain is deposited internationally under the Budapest Treaty and available to the public.

Examples of the genus *Arthrobacter* include *Arthrobacter globiformis* (for example, ATCC8010, ATCC4336, ATCC21056, ATCC31250, ATCC31738 and ATCC35698). These strains are deposited internationally under the Budapest Treaty and available to the public.

Examples of the genus *Mycobacterium* include *Mycobacterium bovis* (for example, ATCC19210 and ATCC27289). These strains are deposited internationally under the Budapest Treaty and available to the public.

Examples of the genus *Micrococcus* include *Micrococcus freudenreichii* (for example, NO. 239 (FERM P-13221)), *Micrococcus leuteus* (for example, NO. 240 (FERM P-13222)), *Micrococcus ureae* (for example, IAM1010), and *Micrococcus roseus* (for example, IFO3764).

The coryneform bacteria may be, let alone a wild type, a mutant thereof or an artificial recombinant thereof. Examples thereof include disruptants in which a gene of lactate dehydrogenase, phosphoenoipyruvate carboxylase, or malate dehydrogenase is disrupted. Among them, preferred is a disruptant in which a lactate dehydrogenase gene is disrupted. In the disruptant, the lactate dehydrogenase gene is disrupted and the metabolic pathway from pyruvic acid to lactic acid is blocked. Particularly preferred is a disruptant of *Corynebacterium glutamicum*, especially the R (FERM BP-18976) strain in which the lactate dehydrogenase gene is disrupted.

Such a disruptant can be prepared based on a conventional gene engineering process. Such a lactate dehydrogenase disruptant and the preparation process thereof are described in WO 2005/010182 A1, for example.

The inventors found that, as shown in FIG. 1, coryneform bacteria have extremely higher 4-HBA resistance compared with other bacteria. Compared with other aerobic bacteria, coryneform bacteria are more resistant to lysis. In this regard, coryneform bacteria are suitable for the 4-HBA production by the method of the present invention.

Construction of Vector for Transformant

The DNA which encodes chorismate-pyruvate lyase is amplified by PCR and then cloned into a suitable vector which is replicable in a host.

The plasmid vector may be any plasmid vector as long as it comprises a gene responsible for autonomously replicating function in a coryneform bacterium. Specific examples of the plasmid vector include pAM330 of *Brevibacterium lactofermentum* 2256 (JP 58-67696 A; Miwa, K. et al., Cryptic plasmids in glutamic acid-producing bacteria. Agric. Biol. Chem. 48: 2901-2903 (1984); and Yamaguchi, R. et al., Determination of the complete nucleotide sequence of the *Brevibacterium lactofermentum* plasmid pAM 330 and the analysis of its genetic information. Nucleic Acids Symp. Ser. 16: 265-267 (1985)), pHM1519 of *Corynebacterium glutamicum* ATCC3058 (Miwa, K. et al., Cryptic plasmids in glutamic acid-producing bacteria. Agric. Biol. Chem. 48:2901-2903 (1584)), pCRY30 of the same *Corynebacterium glutamicum* ATCC3058 (Kurusu, Y. et al., Identification of plasmid partition function in coryneform bacteria. Appl. Environ. Microbiol. 57: 755-764 (1591)), pCG4 of *Corynebacterium glutamicum* T250 (JP 57-183795 A; and Katsumata, R. et al., Protoplast transformation of glutamate-producing bacteria with plasmid DNA. J. Bacteriol., 159: 306-311 (1984)), pAG1, pAG3, pAG14, and pAG50 of the same *Corynebacterium glutamicum* T250 (JP 62-166890 A), pEK0, pEC5, and pEKEx1 of the same *Corynebacterium glutamicum* T250 (Eikmanns, B. J. et al., A family of *Corynebacterium glutamicum*/*Escherichia coli* shuttle vectors for cloning, controlled, gene expression, and promoter probing. Gene, 102: 93-93 (1991)), etc.

Examples of a preferred promoter include promoter PgapA as a promoter of the glyceraldehyde-3-phosphate dehydrogenase A gene (gapA), promoter Pmdh as a promoter of the malate dehydrogenase gene (mdh), and promoter PldhA as a promoter of lactate dehydrogenase A gene (ldhA), all of which are of *Corynebacterium glutamicum* R, and inter alia, PgapA is preferred.

Examples of a preferred terminator include terminator rrnB T1T2 of *Escherichia coli* rRNA operon, terminator trpA of *Escherichia coli*, and terminator trp of *Brevibacterium lactofermentum*, and inter alia, terminator rrnB T1T2 is preferred.

Transformation

As a method of transformation, any publicly known method can be used without limitation. Examples of such a known method include the calcium chloride/rubidium chloride method, the calcium phosphate method, DEAE-dextran transfection, and electroporation. Among them, preferred for a coryneform bacterium is electroporation, which can be performed by a known method (Kurusu, Y. et al., Electroporation-transformation system for Coryneform bacteria by auxotrophic complementation, Agric. Biol. Chem. 54: 443-447 (1990)).

The transformant is cultured using a culture medium usually used for culture of microorganisms. The culture medium may be a natural medium or a synthetic medium containing a carbon source, a nitrogen source, inorganic salts, other nutritional substances, etc.

Examples of the carbon source include carbohydrates and sugar alcohols such as glucose, fructose, sucrose, mannose, maltose, mannitol, xylose, arabinose, galactose, starch, molasses, sorbitol and glycerol; organic acids such as acetic acid, citric acid, lactic acid, fumaric acid, maleic acid and gluconic acid; and alcohols such as ethanol and propanol. Only one kind of these carbon sources or a mixture of two or more kinds may be used. The concentration of these carbon sources in the culture medium is usually about 0.1 to 10 w/v %.

Examples of the nitrogen source include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N-Z-amine, protein hydrolysate, amino acid, etc. may also be used. Only one kind of these nitrogen sources or a mixture of two or more kinds may be used. The concentration of these nitrogen sources in the culture medium varies depending on the kind of the nitrogen compound, but is usually 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. Only one kind of these inorganic salts or a mixture of two or more kinds may be used. The concentration of the inorganic salts in the culture medium varies depending on the kind of the inorganic salts, but is usually about 0.1 to 1 w/v %.

Examples of the nutritional substances include, for example, meat extract, peptone, poly peptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium is usually about 0.1 to 10 w/v %. Further, vitamins may be added as needed. Examples of the vitamins include biotin, thiamine, pyridoxine, pantothenic acid, inositol, nicotinic acid, etc.

The pH of the culture medium is preferably about 6 to 8.

Preferable examples of the microbial culture medium include A medium (Xnui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc.

The culture temperature is about 15 to 45° C., and the culture period is about 1 to 7 days.

Disruption or Deletion in Host Chromosomal Gene

In the coryneform bacterium as a host, the 4-hydroxybenzoate hydroxylase gene on the chromosome preferably has a disruption or deletion. Due to the disruption of 4-hydroxybenzoate hydroxylase, the metabolism of 4-HBA produced is inhibited, resulting in an improved 4-HBA productivity and reduced by-products.

Replacement of a gene on the chromosome with the corresponding gene having a disruption or deletion can be achieved by creating a gene with deletion mutation for not producing a normally functioning enzyme protein, and transforming a bacterium with a DNA comprising the mutated gene for homologous recombination between the gene on the chromosome and the mutated gene. An enzyme protein encoded by a gene having a disruption or deletion, even when produced, has a conformation different from that of the wild type, and has no or reduced function. The gene deletion or gene disruption by way of gene substitution through the use of homologous recombination has already been established, and examples thereof include a method using a plasmid containing a temperature sensitive replication origin or a plasmid capable of conjugal transfer, and a method using a suicide vector not having a replication origin in a host (U.S. Pat. No. 6,303,383, JP 05-007491 A).

(3) Process for Producing 4-HBA

4-HBA can be produced by a method comprising a step of reacting the transformant of the present invention described above in a reaction mixture containing at least one starting compound selected from the group consisting of a sugar, a compound that can be metabolized into chorismic acid by the transformant, chorismic acid, and a salt thereof, and a step of recovering 4-HBA from the reaction mixture.

The starting compound must be a compound that can be taken into the transformant and that is easily available for industrial applications, i.e., one abundantly present in plants, for example.

Glucose is preferred as the sugar, but other sugars that are metabolized into glucose can also be used. Such sugars include oligosaccharides and polysaccharides that have a glucose unit. Examples of such sugars include monosaccharides, such as fructose, mannose, arabinose, xylose, and galactose; disaccharides, such as cellobiose, sucrose, lactose, maltose, trehalose, cellobiose, and xylobiose; polysaccharides, such as dextrin and soluble starch; etc.

Examples of the compound that can be metabolized into chorismic acid include quinic acid, shikimic acid, and the like.

Also, molasses, which contains these starting compounds, can also be used, for example. In addition, a saccharified solution which is obtainable by saccharifying, using a diastatic enzyme, non-edible agricultural waste including straw (rice straw, barley straw, wheat straw, rye straw, oat straw, etc.), bagasse, and corn stover; energy crops including switchgrass, napier grass, and Miscanthus; wood waste; waste paper; etc. and which contains two or more kinds of sugars, including glucose, can also be used. Among the above-mentioned starting compounds, glucose, chorismic acid, quinic acid, and shikimic acid are preferred.

Growth of Microorganism

Before the reaction, the transformant is preferably cultured and grown under aerobic conditions at about 25 to 38° C. for about 12 to 48 hours.

Culture Medium

The culture medium used for aerobic culture of the transformant before the reaction may be a natural medium or a synthetic medium containing a carbon source, a nitrogen source, inorganic salts, other nutritional substances, etc.

Examples of the carbon source that can be used include sugars (monosaccharides such as glucose, fructose, mannose, xylose, arabinose, and galactose; disaccharides such as sucrose, maltose, lactose, cellobiose, xylobiose, and trehalose; polysaccharides such as starch; and molasses); sugar alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin.

Only one kind of these carbon sources or a mixture of two or more kinds may be used.

Examples of the nitrogen source that can be used include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N-Z-amine, protein hydrolysate, amino acid, etc. may also be used. Only one kind of these nitrogen sources or a mixture of two or more kinds may be used. The concentration of these nitrogen sources in the culture medium varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. Only one kind of these inorganic salts or a mixture of two or more kinds may be used. The concentration of the inorganic salts in the culture medium varies depending on the kind of the inorganic salts, but is usually about 0.01 to 1 w/v %.

Examples of the nutritional substances include meat extract, peptone, poly peptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %.

Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 6 to 8.

Specific examples of the preferable culture medium for coryneform bacteria include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc. Such a culture medium can be used after prepared so as to contain a sugar at a concentration in the above-mentioned range.

Reaction Mixture

The reaction mixture may be a natural or synthetic reaction mixture containing a carbon source, a nitrogen source, inorganic salts, other nutritional substances, etc.

The carbon source may be one or more of the above-described starting compounds, or a molasses or a saccharified solution containing such compounds. As the carbon source, besides sugars, sugar alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin can also be used.

Only one kind of these carbon sources or a mixture of two or more kinds may be used.

The concentration of the starting compound in the reaction mixture is preferably about 1 to 20 w/v %, more preferably about 2 to 10 w/v %, and still more preferably about 2 to 5 w/v %.

The total concentration of the carbon sources including the starting compound in the reaction mixture is usually about 2 to 5 w/v %.

Examples of the nitrogen source that can be used include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N-Z-amine, protein hydrolysate, amino acid, etc. may also be used. Only one kind of these nitrogen sources or a mixture or two or more kinds may be used. The concentration of these nitrogen sources in the reaction mixture varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. Only one kind of these inorganic salts or a mixture of two or more kinds may be used. The concentration of the inorganic salts in the reaction mixture varies depending on the kind of the inorganic salts, but is usually about 0.01 to 1 w/v %.

Further, vitamins may be added as needed. Examples of the vitamins include biotin, thiamine (vitamin B1), pyridoxine (vitamin B6), pantothenic acid, inositol, nicotinic acid, etc. The pH of the reaction mixture is preferably about 6 to 8.

Specific examples of the preferable reaction mixture for coryneform bacteria include the above-mentioned BT medium, etc. Such a culture medium can be used after prepared so as to contain a sugar at a concentration in the above-mentioned range.

Reaction Conditions

The reaction temperature, that is, the temperature for keeping the transformant alive during the reaction is preferably about 20 to 50° C., and more preferably about 25 to 47° C. When the temperature is in the above range, 4-HBA can be efficiently produced.

The reaction period is preferably about 1 to 7 days, and more preferably about 1 to 3 days.

The culture may be a batch process, a fed-batch process, or a continuous process. Among them, a batch process is preferred.

The reaction may be performed under aerobic conditions or reducing conditions. The 4-HBA production ability of the transformant of the present invention itself is higher under aerobic conditions. However, aerobic conditions favor the growth of the transformant and the starting compound is consumed for the growth. Accordingly, the 4-HBA production efficiency is lowered.

Therefore, it is preferred that the reaction is performed under aerobic conditions where the transformant does not grow. In the present invention, "does not grow" includes "substantially does not grow" and "hardly grows". For example, growth of the transformant can be avoided or inhibited by the use of a reaction mixture that has a deficiency or limitation in one or more of compounds essential for the growth of the microorganism, for example, vitamins, such as biotin and thiamine, nitrogen sources, etc.

Under reducing conditions, coryneform bacteria substantially do not grow, and therefore, the starting compound is not consumed for the growth, which leads to a higher 4-HBA production efficiency.

The "reducing conditions" is defined based on the oxidation-reduction potential of the reaction mixture. The oxidation-reduction potential of the reaction mixture is preferably about −200 mV to −500 mV, and more preferably about −150 mV to −500 mV.

The reducing conditions of the reaction mixture can be simply estimated using resazurin indicator (in reducing conditions, decolorization from blue to colorless is observed). However, for precise measurement, a redox-potential meter (for example, CRP Electrodes made by BROADLEY JAMES) is used.

As a method of preparing a reaction mixture under reducing conditions, any publicly known method can be used without limitation. For example, as a liquid medium for preparation of the reaction mixture, an aqueous solution for a reaction mixture may be used instead of distilled water or the like. As reference for preparation of the aqueous solution for a reaction mixture, for example, the method for preparing a culture medium for strictly anaerobic microorganisms, such as sulfate-reducing microorganisms (Pfennig, N. et al.: The dissimilatory sulfate-reducing bacteria, In The Prokaryotes, A Handbook on Habitats, Isolation and Identification of Bacteria, Ed. by Starr, M. P. et al. Berlin, Springer Verlag, 926-940, 1981, or *Nogeikagaku Jikkensho*, Ed. by Kyoto Daigaku Nogakubu Nogeikagaku Kyoshitsu, Vol. 3, Sangyo Tosho, 1990, Issue 26) may be used, and such a method provides an aqueous solution under desired reducing conditions.

Specifically, by treating distilled water or the like with heat or under reduced pressure for removal of dissolved gases, an aqueous solution for a reaction mixture under reducing conditions can be obtained. In this case, for removal of dissolved gases, especially dissolved oxygen, distilled water or the like may be treated under reduced pressure of about 10 mmHg or less, preferably about 5 mmHg or less, more preferably about 3 mmHg or less, for about 1 to 60 minutes, preferably for about 5 to 40 minutes.

Alternatively, by adding a suitable reducing agent (for example, thioglycolic acid, ascorbic acid, cysteine hydrochloride, mercaptoacetic acid, thiol acetic acid, glutathione, sodium sulfide, etc.), an aqueous solution for a reaction mixture under reducing conditions can be prepared.

These methods may be suitably combined to prepare an effective aqueous solution for a reaction mixture under reducing conditions.

In the case of a reaction under reducing conditions, it is preferred to maintain the reducing conditions of the reaction mixture during the reaction. For maintenance of reducing conditions, it is preferred that oxygen from the outside of the reaction system is prevented to the utmost extent from entering the system. Specific examples of the method employed for this purpose include a method comprising encapsulating the reaction system with inert gas, such as nitrogen gas, carbon dioxide gas, etc. In some cases, for allowing the metabolic functions in the cells of the aerobic bacterium of the present invention to work effectively during the reaction, addition of a solution of various nutrients or a reagent solution for adjusting and maintaining the pH of the reaction system may be needed. In such a case, for more effective prevention of oxygen incorporation, it is effective to remove oxygen in the solutions to be added, in advance.

Recovery of 4-HBA

Through the culture performed in the above manner, 4-HBA is produced in the reaction mixture. 4-HBA can be recovered by collecting the reaction mixture, and it is also feasible to isolate 4-HBA from the reaction mixture by a known method. Examples of such a known method include the crystallization method, the membrane separation method, the organic solvent extraction method, various adsorption methods (using an ion-exchange resin, synthetic adsorbent, or the like), etc.

(4) Method for Improving Chorismate-Pyruvate Lyase Activity

The present invention includes a method for improving or enhancing chorismate-pyruvate lyase activity, the method comprising replacing (A) valine at position 80 in a chorismate-pyruvate lyase (ubiC) from *Pantoea ananatis* consisting of the amino acid sequence of SEQ ID NO: 1, or (B) an amino acid in another chorismate-pyruvate lyase, the amino acid being at a position enzymologically homologous with that of the above valine, with one or more other amino acids.

Chorismate-pyruvate lyases and the method for mutation thereof are as described above.

The present invention encompasses embodiments in which various constituent features described above are combined within the technical scope of the present invention in such a manner that the effect of the present invention is exerted.

EXAMPLES

Hereinafter, the present invention will be illustrated in more detail by Examples, but it is not limited thereto. Various modifications can be made within the technical idea of the present invention by those with ordinary skill in the art.

Example 1

Cloning of 4-HBA-Producing Gene and Construction of Expression Systems (Wild Type And Mutants)

(1) Extraction of Chromosomal DNA from *Pantoea ananatis*

To extract chromosomal DNA from *Pantoea ananatis* LMG 20103, the bacterium was inoculated into LMG Bacteria Culture Medium No. 1 (1 g of beef extract, 2 g of yeast extract, 5 g of peptone, and 5 g of NaCl were dissolved in 1 L of distilled water, and the pH was adjusted to 7.4) using a platinum loop, and cultured with shaking at 28° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

(2) Cloning of 4-HBA-Producing Gene of *Pantoea ananatis*

A DNA fragment comprising the ubiC gene which encodes a 4-hydroxybenzoic acid-producing gene (chorismate-pyruvate lyase gene) was amplified by the PCR method as described below.

In the PCR, the set of primers shown below was synthesized based on SEQ ID NO: 10 (*Pantoea ananatis* ubiC gene), and used for cloning of the ubiC gene.

Primers for *Pantoea ananatis* ubiC gene amplification (SEQ ID NO: 19)
(a-1); 5'-CTCTCATATGACGCAAGACCCGCT-3'

(SEQ ID NO: 20)
(b-1); 5'-CTCTCATATGTTAACCTTGATCACGATAGAGCG-3'

Primers (a-1) and (b-1) each have an NdeI restriction enzyme site added thereto.

Actual PCR was performed using a Veriti thermal cycler (made by Applied Biosystems) and PrimeSTAR GXL DNA Polymerase (made by Takara Bio, Inc.) as a reaction reagent under the conditions described below.

Reaction Mixture:

| | |
|---|---|
| PrimeSTAR GXL DNA Polymerase (1.25 U/μL) | 1 μL |
| 5× PrimeSTAR GXL Buffer ($Mg^{2+}$ plus) | 10 μL |
| dNTP Mixture (2.5 mM each) | 4 μL |
| Template DNA | 1 μL (DNA content: 1 μg or less) |
| The above 2 primers*) | 1 μL each (final conc.: 0.2 μM) |
| Sterile distilled water | 32 μL |

The above ingredients were mixed, and 50 μL of the reaction mixture was subjected to PCR.

PCR Cycle:
Denaturation step: 98° C., 10 seconds
Annealing step: 50° C., 5 seconds
Extension step: 68° C., 31 seconds
A cycle consisting of the above 3 steps was repeated 30 times.

Using 10 μL of the above-produced reaction mixture, 0.8% agarose gel electrophoresis was performed, and an about 0.5-kb DNA fragment of the ubiC gene of *Pantoea ananatis* was detected. The DNA fragment was purified using NucleoSpin Gel and PCR Clean-Up (made by Takara Bio, Inc.).

(3) Construction of 4-hydroxybenzoic Acid-Producing Gene (Chorismate-Pyruvate Lyase Gene) Expression Plasmid 10 μL of the about 0.5-kb DNA fragment comprising the ubiC gene of *Pantoea ananatis* amplified by the PCR in the above (2) and 2 μL of the cloning vector pCRB209 (WO 2012/033112) comprising a promoter PgapA were each cut with the use of restriction enzyme NdeI and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume, was 10 μL, and the mixture was allowed to react at 1.5° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture medium and cut using the restriction enzyme, to confirm the inserted fragment. As a result, in addition to an about 5.1-kb DNA fragment of the plasmid pCRB209, an about 0.5-kb inserted fragment of the ubiC gene of *Pantoea ananatis* was confirmed.

The plasmid comprising the ubiC gene of *Pantoea ananatis* was named pHBA22.

(4) Construction of Transgenic Strains for 4-hydroxybenzoic Acid-Producing Gene (Chorismate-Pyruvate Lyase Gene)

Using the above-described plasmid pHBA22, transformation of *Corynebacterium glutamicum* R was performed by electroporation [Agric. Biol. Chem., Vol. 54, 443-447 (1990) and Res. Microbiol., Vol. 144, 181-185 (1993)], and the transgenic strain was applied to A agar medium containing 50 μg/mL of kanamycin.

A growing strain on the culture medium was subjected to liquid culture in the usual manner. Plasmid DNA was extracted from the culture and cut with the use of a restriction enzyme to confirm the inserted plasmid. As a result, introduction of the above-constructed plasmid pHBA22 was confirmed.

The obtained strain was named *Corynebacterium glutamicum* HBA-22.

(5) Construction of Transgenic Plasmids for 4-hydroxybenzoic Acid-Producing Genes (Chorismate-Pyruvate Lyase Genes) with Mutation by Site-Directed Mutagenesis Using the above-described plasmid pHBA22, two mutants having different kinds of amino acids in place of the amino acid at the V80 site were prepared by Inverse PCR, and the obtained site-specific transgenic plasmids were named pHBA23 and pHBA24.

In the PCR, the set of primers shown below was synthesized based on SEQ ID NO: 10 (*Pantoea ananatis* ubiC gene), and used for introduction of mutation to the V80 site of the ubiC gene.

```
Primers for mutation of Pantoea anana-
tis ubiC
gene
                                      (SEQ ID NO: 21)
(a-2); 5'-CGAGAAgcaATTCTCTACGGGGATG-3'

(SEQ ID NO: 22)
(b-2); 5'-CAGCCAGAAACGCTGATCG-3'

(SEQ ID NO: 23)
(a-3); 5'-tgcATTCTCTACGGGGATGAGG-3'

(SEQ ID NO: 24)
(b-3); 5'-TTCTCGCAGCCAGAAACGCTG-3'
```

Actual PCR was performed using a Veriti thermal cycler (made by Applied Biosystems) and PrimeSTAR GXL DNA Polymerase (made by Takara Bio, Inc.) as a reaction reagent under the conditions described below.
Reaction Mixture:

| | |
|---|---|
| PrimeSTAR GXL Data Polymerase (1.25 U/μL) | 1 μL |
| 5× PrimeSTAR GXL Buffer ($Mg^{2+}$ plus) | 10 μL |
| dNTP Mixture (2.5 mM each) | 4 μL |
| Template DNA | 1 μL (DNA content: 1 μg or less) |
| The above 2 primers*) | 1 μL each (final conc.: 0.2 μM) |
| Sterile distilled water | 32 μL |

The above ingredients were mixed, and 50 μL of the reaction mixture was subjected to PCR.
*)For amplification of pHBA23 (V80A), a combination of primers (a-2) and (b-2), and for amplification of pHBA24 (V80C), a combination of primers (a-3) and (b-3) were used.

PCR Cycle:
Denaturation step: 98° C., 10 seconds
Annealing step: 50° C., 5 seconds
Extension step: 68° C., 338 seconds
A cycle consisting of the above 3 steps was repeated 30 times.

Using 10 μL each of the above-produced reaction mixtures, 0.8% agarose gel electrophoresis was performed, and an about 5.6-kb DNA fragment of the ubiC gene of *Pantoea ananatis* was detected in both cases. The DNA fragment was purified using NucleoSpin Gel and PCR Clean-Up (made by Takara Bio, Inc.).

The purified amplification product was phosphorylated using T4 Polynucleotide Kinase (made by Takara Bio, Inc.) and then purified using NucleoSpin Gel and PCR Clean-Up (made by Takara Bio, Inc.). The obtained phosphorylated DNA fragment was allowed to self-ligate using the DNA Ligation Kit (made by Takara Bio, Inc.). Using the obtained ligation liquid, *Escherichia coli* HST02 was transformed by the calcium chloride method (J. Mol. Biol. 53: 159-162 (1970)) and was applied to LB agar medium (1% polypeptone, 0.5% yeast extract, 0.5% sodium chloride, and 1.5% agar) containing 50 μg/mL of kanamycin. A growing strain on the culture medium was subjected to liquid culture in the usual manner. Plasmid DNA was extracted from the culture, and the introduction of the mutation into the V80 of the ubiC gene was confirmed by the sequence analysis of the plasmid.

The obtained plasmids were named pHBA23 and pHBA24. The outline of gene recombination of the plasmids is shown in Table 1.

TABLE 1

Transgenic plasmids (wild-type and mutants) for 4-HBA-producing gene of *Pantoea ananatis*

| Plasmid | Type of introduced mutation | Amino acid at position 80 | Codon at position 80 |
|---|---|---|---|
| pHBA22 | None (wild type) | valine | gtc |
| pHBA23 | V80A | alanine | gca |
| pHBA24 | V80C | cysteine | tgc |

(6) Construction of Transgenic Strains for 4-hydroxybenzoic Acid-Producing Gene (Chorismate-Pyruvate Lyase Gene)

Using the above-described plasmids pHBA22 to pHBA24, transformation of *Corynebacterium glutamicum* R was performed by electroporation (Agric. Biol. Chem., Vol. 54, 443-447 (1990) and Res. Microbiol., Vol. 144, 181-185 (1993)), and each of the transgenic strains was applied to A agar medium containing 50 Hg/mL of kanamycin.

A growing strain on the culture medium was subjected to liquid culture in the usual manner. Plasmid DNA was extracted from the culture and cut with the use of a restriction enzyme to confirm the inserted plasmid. As a result, introduction of the above-constructed plasmids pHBA22 to pHBA24 was confirmed.

The obtained strains were named *Corynebacterium glutamicum* HBA-22 to HBA-24. The outline of gene recombination in the above-obtained strains is shown in Table 2.

TABLE 2

Transgenic strains for 4-HBA-producing gene (mutant) of *Pantoea ananatis*

| Strain | Host strain | Type of introduced mutation | Amino acid at position 80 |
|---|---|---|---|
| HBA22 | *Corynebacterium glutamicum* R | None (wild type) | valine |
| HBA23 | | V80A | alanine |
| HBA24 | | V80C | cysteine |

Example 2

Comparison of Chorismate-Pyruvate Lyase Activity Among *Corynebacterium glutamicum* 4-hydroxybenzoic Acid-Producing Gene Transgenic Strains Using the cell lysates obtained by sonication of *Corynebacterium glutamicum* HBA-22 (V80, wild type), HBA-23 (V80A), and HBA-24 (V80C) prepared in Example 1, comparison of the chorismate-pyruvate lyase activity was performed.

Specifically, each of the above strains was applied to A agar medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 ml of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) containing 50 μg/mL of kanamycin and was left stand in the dark at 33° C. for 15 hours.

An inoculation loop of each strain grown on a plate as above was inoculated into a test tube containing 10 mL of A liquid medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4 \cdot 7H_2O$, 1 mL of 0.06% (w/v) $Fe_2SO_4 \cdot 7H_2O + 0.042\%$ (w/v) $MnSO_4 \cdot 2H_2O$, 1 ml of 0.02% (w/v) biotin solution, 2 mL of 0.01% (w/v) thiamin solution, 2 g of yeast extract, 7 g of vitamin assay casamino acid, and 40 g of glucose were suspended in 1 L of distilled water) containing 50 μg/mL of kanamycin and was aerobically cultured with shaking at 33° C. for 15 hours.

Each kind of the bacterial cells cultured and proliferated as above was collected by centrifugation (8,000 rpm, 4° C., 10 minutes). After disrupting the bacterial cells by sonication, centrifugation (15,000 rpm, 4° C., 20 minutes) was performed. Using the supernatant of the cell lysate as a crude enzyme liquid, chorismate-pyruvate lyase activity was determined by the following method.

The crude enzyme liquid, 50 mM Tris-HCl (pH 7.5), 0.5 mM of chorismate Ba salt, 0.2 mM of NADH, 0.2 M of NaCl and 5 units of lactate dehydrogenase were mixed, the reaction was allowed to proceed at 33° C., and the decrease in absorbance of NADH at 340 nm was monitored to analyze the initial rate of the reaction. From the initial rate of the reaction and the protein concentration, the specific activity was calculated (the amount of the enzyme that produces 1 μmol of 4-HBA per minute was defined as 1 unit). (After the reaction mixture was filtered, the resulting 4-HBA was subjected to HPLC for direct detection of the peak of 4-HBA (Cosmosil C18 ARII made by Nacalai Tesque, mobile phase: 20% methanol and 0.07% perchloric acid) to confirm that the two assay methods were similar in quantitative performance.)

As a result, as shown in Table 3, the V80A mutant and the V80C mutant showed a higher activity as compared with the V80 (wild type) strain.

TABLE 3

Comparison of chorismate-pyruvate lyase activity among transgenic strains for 4-HBA-producing gene (mutant) of *Pantoea ananatis*

| Strain | Host strain | Type introduced mutation | Amino acid at position 80 | Enzymatic activity (mU · mg⁻¹) |
|---|---|---|---|---|
| HBA22 | Corynebacterium glutamicum R | None (wild type) | valine | 339 |
| HBA23 | | V80A | alanine | 485 |
| HBA24 | | V80C | cysteine | 341 |

Example 3

Production of 4-hydroxybenzoic Acid From Glucose Using *Corynebacterium glutamicum* 4-hydroxybenzoic Acid-Producing Gene Transgenic Strains Each of the *Corynebacterium glutamicum* HBA-22 (wild type), HBA-23 (V80A), and HBA-24 (V30C) strains prepared in Example 1 was applied to A agar medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4 \cdot 7H_2O$, 1 mL of 0.06% (w/v) $Fe_2SO_4 \cdot 7H_2O + 0.042\%$ (w/v) $MnSO_4 \cdot 2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) containing 50 μg/mL of kanamycin and was left stand in the dark at 33° C. for 15 hours.

An inoculation loop of each of the *Corynebacterium glutamicum*/4-HBA-producing gene transgenic strains grown on a plate as above was inoculated into a test tube containing 10 mL of A liquid medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4 \cdot 7H_2O$, 1 mL of 0.06% (w/v) $Fe_2SO_4 \cdot 7H_2O + 0.042\%$ (w/v) $MnSO_4 \cdot 2H_2O$, 1 mL of 0.02% (w/v) biotin solution, 2 mL of 0.01% (w/v) thiamin solution, 2 g of yeast extract, 7 g of vitamin assay casamino acid, and 40 g of glucose were suspended in 1 L of distilled water) containing 50 ng/mL of kanamycin and also 2% of calcium carbonate and was aerobically cultured with shaking at 200 rpm at 33° C. for 24 hours.

The culture obtained after the growth under the above-described conditions was centrifuged (15,000 rpm at 4° C. for 10 minutes), and the obtained supernatant was used for quantitative determination of 4-HBA by HPLC.

As a result, as shown in Table 4, the HBA-23 (V80A) and HBA-24 (V80C) strains produced 4-HBA at an about 2.3 times higher concentration and an about 1.6 times higher concentration, respectively, as compared with the HBA-22 (wild type) strain.

TABLE 4

Experiment of 4-HBA production from glucose using *Corynebacterium glutamicum* 4-HBA-producing gene transgenic strains (transgenic strains for ubiC gene of *Pantoea ananatis*)

| Strain | Host strain | Origin of 4-hydroxy benzoic acid-producing gene | Type of introduced mutation | Amount of produced 4-hydroxy benzoic acid (mM) (After 24 hours) |
|---|---|---|---|---|
| HBA22 | Corynebacterium glutamicum R | Pantoea ananatis | None (wild | 0.70 |
| HBA23 | | | V80A | 1.64 |
| HBA24 | | | V80C | 1.14 |

Example 4

Extraction of Chromosomal DNA from *Providencia* bacteria, Cloning of 4-hydroxybenzoic Acid-Producing Genes (Chorismate-Pyruvate Lyase Genes), Construction of 4-hydroxybenzoic Acid-Producing Gene Expression Plasmids, Construction of 4-hydroxybenzoic Acid-Producing Gene Transgenic Strains, Construction of Site-Specific Transgenic Strains for 4-hydroxybenzoic Acid-Producing Genes, And Production of 4-hydroxybenzoic Acid from Glucose Using *Corynebacterium glutamicum* Transgenic Strains for 4-hydroxybenzoic Acid-Producing Genes (1) Extraction of Chromosomal DNA from Microorganisms To extract chromosomal DNA from *Providencia stuartii* ATCC 25827, the bacterium was inoculated into ATCC Medium No. 3 (5 g of peptone and 3 g of beef extract were dissolved in 1 L of distilled water, and the pH was adjusted to 6.8) using a platinum loop, and cultured with shaking at 37° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Providencia rustigianii* JCM 3953, the bacterium was inoculated into JCM Medium No. 12 (5 g of peptone, 3 g of beef extract, and 5 g of NaCl were dissolved in 1 L of distilled water, and the pH was adjusted to 7.0) using a platinum loop, and cultured with shaking at 37° C. until the logarithmic growth phase. After the bacterial cells were collected, chromosomal DNA was recovered from the collected cells using a DNA extraction kit (trade name: GenomicPrep Cells and Tissue DNA isolation Kit, made by Amersham) according to the instruction manual.

To extract chromosomal DNA from *Escherichia coli* K12 MG1655, the bacterium was inoculated into LB Medium (10 g of tryptone, 5 g of yeast extract, and 5 g of NaCl were dissolved in 1 L of distilled water) using a platinum loop, and cultured with shaking at 37° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Cronobacter sakazakii* JCM 1233, the bacterium was inoculated into JCM Medium No. 12 (5 g of peptone, 3 g of beef extract, and 5 g of NaCl were dissolved in 1 L of distilled water, and the pH was adjusted to 7.0) using a platinum loop, and cultured with shaking at 37° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

(2) Cloning of 4-hydroxybenzoic Acid-Producing Genes (Chorismate-Pyruvate Lyase Genes)

A DNA fragment comprising the ubiC gene which encodes a 4-hydroxy benzoic acid-producing gene (chorismate-pyruvate lyase gene) was amplified by the PCR method as described below.

In the PCR, the sets of primers shown below were synthesized based on SEQ ID NO: 11 (*Providencia stuartii* ubiC gene), SEQ ID NO: 12 (*Providencia rustigianii* ubiC gene), SEQ ID NO: 17 (*Escherichia coli* ubiC gene), and SEQ ID NO: 18 (*Cronobacter sakazakii* ubiC gene), and used for cloning of the corresponding ubiC genes.

```
Primers for Providencia stuartii ubiC gene
amplification
                                   (SEQ ID NO: 25)
(a-21); 5'-CTCTCATATGGATGAAACGCTTTTTATCTCTCAC-3'

(SEQ ID NO: 26)
(b-21); 5'-CTCTCATATGTCCCTCCATTTGTTGTGCTC-3'
```

Primers (a-21) and (b-21) each have an NdeI restriction enzyme site added thereto.

```
Primers for Providencia rustigianii ubiC gene
amplification
                                   (SEQ ID NO: 27)
(a-22); 5'-CTCTCATATGCATGAAACAATTTTTACCCATCATCC-3'

(SEQ ID NO: 28)
(b-22); 5'-CTCTCATATGGATTATGTTAGATAGTTATCTATATGCA
GGTG-3'
```

Primers (a-22) and (b-22) each have an NdeI restriction enzyme site added thereto.

```
Primers for Escherichia coli ubiC gene amplification
                                   (SEQ ID NO: 29)
(a-23); 5'-CTCTCATATGTCACACCCCGCGTTAA-3'

(SEQ ID NO: 30)
(b-23); 5'-CTCTCATATGTTAGTACAACGGTGACGCC-3'
```

Primers (a-23) and (b-23) each have an NdeI restriction enzyme site added thereto.

```
Primers for Cronobacter sakazakii ubiC gene
amplification
                                   (SEQ ID NO: 31)
(a-24); 5'-CTCTCATATGTCCCATCCCGCGCTGAG-3'

(SEQ ID NO: 32)
(b-24); 5'-CTCTCATATGTATTCTGCGTCAGGCTCCAC-3'
```

Primers (a-24) and (b-24) each have an NdeI restriction enzyme site added thereto.

As the template DNA, chromosomal DNAs extracted from *Providencia rustigianii* JCM 3953, *Providencia stuartii* ATCC 25827, *Escherichia coli* MG1655, and *Cronobacter sakazakii* JCM 1233 were used.

Actual PCR was performed using a Veriti thermal cycler (made by Applied Biosystems) and PrimeSTAR GXL DNA Polymerase (made by Takara Bio, Inc.) as a reaction reagent under the conditions described below.

Reaction Mixture:

| | |
|---|---|
| PrimeSTAR GXL DNA Polymerase (1.25 U/μL) | 1 μL |
| 5× PrimeSTAR GXL Buffer (Mg$^{2+}$ plus) | 10 μL |
| dNTP Mixture (2.5 mM each) | 4 μL |
| Template DNA | 1 μL (DNA content: 1 μg or less) |
| The above 2 primers*) | 1 μL each (final conc.: 0.2 μM) |
| Sterile distilled water | 32 μL |

The above ingredients were mixed, and 50 μL of the reaction mixture was subjected to PCR.
*)For amplification of the ubiC gene of *Providencia stuartii*, a combination of primers (a-21) and (b-21); for amplification of the ubiC gene of *Providencia rustigianii*, a combination of primers (a-22) and (b-22); for amplification of the ubiC gene of *Escherichia coli*, a combination of primers (a-23) and (b-23); and for amplification of the ubiC gene of *Cronobacter sakazakii*, a combination of primers (a-24) and (b-24) were used.

PCR Cycle:

Denaturation step: 98° C., 10 seconds
Annealing step: 50° C., 5 seconds
Extension step: 68° C.
*Providencia stuartii* ubiC gene, 32 seconds
*Providencia rustigianii* ubiC gene, 31 seconds
*Escherichia coli* ubiC gene, 30 seconds
*Cronobacter sakazakii* ubiC gene, 32 seconds A cycle consisting of the above 3 steps was repeated 30 times.

Using 10 μL each of the above-produced reaction mixtures, 0.8% agarose gel electrophoresis was performed. As a result, detected were an about 0.5-kb DNA fragment in the case of the ubiC gene of *Providencia stuartii*, in the case of the ubiC gene of *Providencia rustigianii*, and in the case of the ubiC gene of *Escherichia coli*; and an about 0.6-kb DNA fragment in the case of the ubiC gene of *Cronobacter sakazakii*. Each DNA fragment was purified using NucleoSpin Gel and PCR Clean-Up (made by Takara Bio, Inc.).

(3) Construction of 4-hydroxybenzoic Acid-Producing Gene (Chorismate-Pyruvate Lyase Gene) Expression Plasmids 10 μL of the about 0.5-kb DNA fragment comprising the ubiC gene of *Providencia stuartii*, the ubiC gene of *Providencia rustigianii*, or the ubiC gene of *Escherichia coli*; or the about 0.6-kb DNA fragment comprising the ubiC gene of *Cronobacter sakazakii*, each of which was amplified by the PCR as above, and 2 μL of the cloning vector pCRB209 comprising a promoter PgapA (WO 2012/033112) were each cut using the restriction enzyme NdeI and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation.

Using the obtained ligation liquids separately, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 fig/mL of kanamycin.

A growing strain on the culture medium was subjected to liquid culture in the usual manner. Plasmid DNA was extracted from the culture and cut using the restriction enzyme to confirm the inserted fragment. As a result, in addition, to an about 5.1-kb DNA fragment of the plasmid pCRB209, confirmed were an about 0.5-kb inserted fragment in the case of the ubiC gene of *Providencia stuartii*, an about 0.5-kb inserted fragment in the case of the ubiC gene of *Providencia rustigianii*, an about 0.5-kb DNA fragment in the case of the ubiC gene of *Escherichia coli*, and an about 0.6-kb DNA fragment in the case of the ubiC gene of *Cronobacter sakazakii*.

The plasmid comprising the ubiC gene of *Providencia stuartii* was named pHBA42, the plasmid comprising the ubiC gene of *Providencia rustigianii* was named pHBA45, the plasmid comprising the ubiC gene of *Escherichia coli* was named pHBA48, and the plasmid comprising the ubiC gene of *Cronobacter sakazakii* was named pHBA51.

(4) Construction of Transgenic Plasmids for 4-hydroxybenzoic Acid-Producing Genes (Chorismate-Pyruvate Lyase Genes) with Mutation by Site-Directed Mutagenesis Using the above-described plasmid pHBA42, mutants in which the amino acid at the V80 site was replaced with A (alanine) or C (cysteine) were prepared by Inverse PCR, and the obtained site-specific transgenic plasmids were named pHBA43 and pHBA44.

In the PCR, the set of primers shown below was synthesized based on SEQ ID NO: 11 (*Providencia stuartii* ubiC gene), and used for introduction of mutation to the V80 site of the ubiC gene.

```
Primers for mutation of Providencia stuartii ubiC
gene
                                     (SEQ ID NO: 33)
(a-25); 5'-gcaATTATGTATGGTGATAATATTCCATGGTTACTTG-3'

(SEQ ID NO: 34)
(a-26); 5'-tgcATTATGTATGGTGATAATATTCCATGGTTACTTG-3'

(SEQ ID NO: 35)
(b-25); 5'-TTCACGTAACCAATAATATTCACTGACAG-3'
```

Similarly, using the above-described plasmid pHBA45, mutants in which the amino acid at the V80 site was replaced with A (alanine) or C (cysteine) were prepared by Inverse PCR, and the obtained site-specific transgenic plasmids were named pHBA46 and pHBA47.

In the PCR, the set of primers shown below was synthesized based on SEQ ID NO: 12 (*Providencia rustigianii* ubiC gene), and used for introduction of mutation to the V80 site of the ubiC gene.

```
Primer for mutation of Providencia rustigianii
ubiC gene
                                     (SEQ ID NO: 36)
(a-27); 5'-ATTATGTATGGGGATAATATTCCGTGG-3'

(SEQ ID NO: 37)
(b-27); 5'-gcaTTCTCGCAACCAGTAACGTTG-3'

(SEQ ID NO: 38)
(b-28); 5'-tgcTTCTCGCAACCAGTAACGTTG-3'
```

In the PCR, the set of primers shown below was synthesized based on SEQ ID NO: 17 (*Escherichia coli* ubiC gene), and used for introduction of mutation to the 1 (isoleucine) 79 site of the ubiC gene.

```
Primers for mutation of Escherichia coli ubiC
gene
                                     (SEQ ID NO: 39)
(a-29); 5'-gcaTTGTTATGTGCCGATGGTGAAC-3'

(SEQ ID NO: 40)
(a-30); 5'-tgcTTGTTATGTGCCGATGGTGAAC-3'

(SEQ ID NO: 41)
(b-29); 5'-TTCACGTAACCAATAATATTCACTGACAG-3'
```

Similarly, using the above-described plasmid pHBA51, mutants in which the amino acid at the I (isoleucine) 79 site was replaced with A (alanine) or C (cysteine) were prepared by PCR, and the obtained site-specific transgenic plasmids were named pHBA52 and pHBA53.

In the PCR, the set of primers shown below was synthesized based on SEQ ID NO: 18 (*Cronobacter sakazakii* ubiC gene), and used for introduction of mutation to the 179 site of the ubiC gene.

```
Primers for mutation of Cronobacter sakazakii
ubiC gene
                                     (SEQ ID NO: 42)
(a-31); 5'-gcaCTGCTGTGCGGCGACG-3'

(SEQ ID NO: 43)
(a-32); 5'-tgcCTGCTGTGCGGCGACG-3'

(SEQ ID NO: 44)
(b-31); 5'-TTCGCGCAGCCAGTAGCG-3'
```

Actual PCR was performed using a Veriti thermal cycler (made by Applied Biosystems) and PrimeSTAR GXL DNA Polymerase (made by Takara Bio, Inc.) as a reaction reagent under the conditions described below.

Reaction Mixture:

| | |
|---|---|
| PrimeSTAR GXL DNA Polymerase (1.25 U/μL) | 1 μL |
| 5× PrimeSTAR GXL Buffer (Mg$^{2+}$ plus) | 10 μL |
| dNTP Mixture (2.5 mM each) | 4 μL |
| Template DNA | 1 μL (DNA content: 1 μg or less) |
| The above 2 primers*[)] | 1 μL each (final conc.: 0.2 μM) |
| Sterile distilled water | 32 μL |

The above ingredients were mixed, and 50 μL of the reaction mixture was subjected to PCR.

*[)]For amplification of pHBA43, a combination of primers (a-25) and (b-25); for amplification of pHBA44, a combination of primers (a-26) and (b-25); for amplification of pHBA46, a combination of primers (a-27) and (b-27); for amplification of pHBA47, a combination of primers (a-27) and (b-28); for amplification of pHBA49, a combination of primers (a-29) and (b-29); for amplification of pHBA50, a combination of primers (a-30) and (b-29); for amplification of pHBA52, a combination of primers (a-31) and (b-31); and for amplification of pHBA53, a combination of primers (a-32) and (b-31) were used.

PCR Cycle:

Denaturation step: 98° C., 10 seconds

Annealing step: 50° C., 5 seconds

Extension step: 68° C.

*Providencia stuartii* (pHBA43, pHBA44), 339 seconds

*Providencia rustigianii* (pHBA46, pHBA47), 338 seconds

*Escherichia coli* (pHBA49, pHBA50), 337 seconds

*Cronobacter sakazakii* (pHBA52, pHBA53), 339 seconds

A cycle consisting of the above 3 steps was repeated 30 times.

Using 10 μL each of the above-produced reaction mixtures, 0.8% agarose gel electrophoresis was performed. As a result, detected were an about 5.7-kb DNA fragment in the case of the ubiC gene of *Providencia stuartii*, an about 5.6-kb DNA fragment in the case of the ubiC gene of *Providencia rustigianii*, an about 5.6-kb DNA fragment in the case of the ubiC gene of *Escherichia coli*, and an about 5.7-kb DNA fragment in the case of the ubiC gene of *Cronobacter sakazakii*. Each DNA fragment was purified using NucleoSpin Gel and PCR Clean-Up (made by Takara Bio, Inc.).

The purified amplification product was phosphorylated using T4 Polynucleotide Kinase (made by Takara Bio, Inc.) and then purified using NucleoSpin Gel and PCR Clean-Up (made by Takara Bio, Inc.). The obtained phosphorylated DNA fragment was allowed to self-ligate using the DNA Ligation Kit (made by Takara Bio, Inc.). Using the obtained ligation liquid, *Escherichia coli* HST02 was transformed by the calcium chloride method (J. Mol. Biol. 53: 159-162 (1970)) and was applied to LB agar medium (1% polypeptone, 0.5% yeast extract, 0.5% sodium chloride, and 1.5% agar) containing 50 μg/mL of kanamycin. A growing strain on the culture medium was subjected to liquid culture in the usual manner. Plasmid DNA was extracted from the culture, and the introduction of the mutation into the V80 or I79 site of the ubiC gene was confirmed by the sequence analysis of the plasmid.

The obtained plasmids were named pHBA43, pHBA44, pHBA46, pHBA47, pHBA49, pHBA50, pHBA52, and pHBA53. The outline of gene recombination of the plasmids is shown in Table 5.

TABLE 5

Transgenic plasmids for 4-HBA-producing gene (WT and mutants)

| Plasmid | Origin of ubiC gene | Type of introduced mutation* | Codon used |
|---|---|---|---|
| pHBA42 | *Providencia* | Wild type (V80) | gtc |
| pHBA43 | *stuartii* | V80A | gca |
| pHBA44 | | V80C | tgc |
| pHBA45 | *Providencia* | Wild type (V80) | gtc |
| pHBA46 | *rustigianii* | V80A | gca |
| pHBA47 | | V80C | tgc |
| pHBA48 | *Escherichia coli* | Wild type (I79) | att |
| pHBA49 | | I79A | gca |
| pHBA50 | | I79C | tgc |
| pHBA51 | *Cronobacter* | Wild type (I79) | atc |
| pHBA52 | *sakazakii* | I79A | gca |
| pHBA53 | | I79C | tgc |

In the column of the "Type of introduced mutation*", A means "a mutation to alanine", and C means "a mutation to cysteine". Also, V means "a mutation of valine", and I means "a mutation of isoleucine". In addition, 80 means "position 80" and 79 means "position 79".

(5) Construction of Transgenic Strains for 4-hydroxybenzoic Acid-Producing Gene (Chorismate-Pyruvate Lyase Gene)

Using the above-described plasmids pHBA42, pHBA43, pHBA44, pHBA45, pHBA46, pHBA47, pHBA48, pHBA49, pHBA50, pHBA51, pHBA52, and pHBA53, transformation of *Corynebacterium glutamicum* R was performed by electroporation [Agric. Biol. Chem., Vol. 54, 443-447 (1590) and Res. Microbiol., Vol. 144, 181-185 (1993)], and each of the transgenic strains was applied to A agar medium containing 50 μg/mL of kanamycin.

A growing strain on the culture medium was subjected to liquid culture in the usual manner. Plasmid DNA was extracted from the culture and cut with the use of a restriction enzyme to confirm the inserted plasmid. As a result, introduction of the above-prepared plasmids pHBA42, pHBA43, pHBA44, pHBA45, pHBA46, pHBA47, pHBA48, pHBA49, pHBA50, pHBA51, pHBA52, and pHBA53 was confirmed.

The obtained strains were named *Corynebacterium glutamicum* HBA42, HBA43, HBA44, HBA45, HBA46, HBA47, HBA48, HBA45, HBA50, HBA51, HBA52, and HBA53. The outline of gene recombination of the plasmids is shown in Table 6.

TABLE 6

Transgenic strains for 4-HBA-producing gene (mutant)

| Strain | Host strain | Plasmid | Origin of ubiC gene | Type of introduced mutation* |
|---|---|---|---|---|
| HBA42 | *Corynebacterium* | pHBA42 | *Providencia* | Wild type |
| HBA43 | *glutamicum* R | pHBA43 | *stuartii* | V80A |
| HBA44 | | pHBA44 | | V80C |
| HBA45 | | pHBA45 | *Providencia* | Wild type |
| HBA46 | | pHBA46 | *rustigianii* | V80A |
| HBA47 | | pHBA47 | | V80C |
| HBA48 | | pHBA48 | *Escherichia* | Wild type |
| HBA49 | | pHBA49 | *coli* | I79A |
| HBA50 | | pHBA50 | | I79C |
| HBA51 | | pHBA51 | *Cronobacter* | Wild type |
| HBA52 | | pHBA52 | *sakazakii* | I79A |
| HBA53 | | pHBA53 | | I79C |

In the column of the "Type of introduced mutation*", A means "a mutation to alanine", and C means "a mutation to cysteine". Also, V means "a mutation of valine", and I means "a mutation of isoleucine". In addition, 80 means "position 80" and 79 means "position 79".

Each of the *Corynebacterium glutamicum*/4-HBA-producing gene transgenic strains obtained as above (HBA42, HBA43, HBA44, HBA45, HBA46, HBA47, HBA48, HBA49, HBA50, HBA51, HBA52, and HBA53) was applied to A agar medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.0.1% (w/v) thiamin solution, 2 g of yeast extract, 7 g of vitamin assay casamino acid, 40 g of glucose, and 15 g of agar were suspended in 1 L of distilled water) containing 50 μg/mL of kanamycin and was left stand in the dark at 33° C. for 15 hours.

An inoculation loop of each of the *Corynebacterium glutamicum*/4-HBA-producing gene transgenic strains grown on a plate as above was inoculated into a test tube containing 10 mL of A liquid medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+ 0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, and 40 g of glucose were suspended in 1 L of distilled water) containing 50 μg/mL of kanamycin and also 2% of calcium carbonate and was aerobically cultured with shaking at 33° C. for 24 hours.

The culture obtained after the growth under the above-described conditions was centrifuged (15,000 rpm at 4° C. for 10 minutes), and the obtained supernatant was used for quantitative determination of 4-HBA by HPLC.

As the results in Table 7 show, each of the strains of *Corynebacterium glutamicum* HBA-42 to 53 produced the aimed 4-HBA. Among the transgenic strains for ubiC gene from *Providencia stuartii*, HBA-43 (V80A) and HBA-44 (V30C) had an enhanced, i.e., superior 4-HBA-producing ability, as compared with HBA-42 (wild type). Among the transgenic strains for ubiC gene from *Providencia rettgeri*, HBA-46 (V80A) and HBA-47 (V80C) had an enhanced, i.e., superior 4-HBA-producing ability, as compared with HBA-45 (wild type). Among the transgenic strains for ubiC gene from *Escherichia coli*, HBA-49 (I79A) and HBA-50 (I79C) had an enhanced, i.e., superior 4-HBA-producing ability, as compared with HBA-48 (wild type).

Among the transgenic strains for ubiC gene from *Cronobacter sakazakii*, HBA-52 (I79A) and HBA-53 (I79C) had an enhanced, i.e., superior 4-HBA-producing ability, as compared with HBA-51 (wild type). Using *Corynebacterium glutamicum* wild strain (as a control having an empty vector only), a similar experiment was conducted. In this case, 4-HBA production was not observed.

The strain highly expressing the V80C mutant of the ubiC gene of *Providencia rustigianii* (HBA-47) showed the highest 4-HBA-production in the culture supernatant.

As shown above, based on the analysis of ubiC mutants of *Pantoea ananatis*, *Providencia stuartii*, *Providencia rustigianii*, and *Cronobacter sakazakii*, it was revealed that a mutation at V80 (V80A, V80C) enhances chorismate-pyruvate lyase activity.

Similarly, in the cases of ubiC genes of *Escherichia coli* and *Cronobacter sakazakii*, of which the amino acid residue 179 is known to correspond to the above V80 based on the results of homology comparison, it was revealed that a similar mutation at the site (I79A, I79C) enhances chorismate-pyruvate lyase activity. Also, it was demonstrated that the mutation at the site is an important mutation leading to the activity enhancement of various types of chorismate-pyruvate lyase, and that a recombinant strain of *Corynebacterium glutamicum* in which the mutant is highly expressed has an enhanced 4-HBA-producing ability.

TABLE 7

Experiment of 4-HBA production from glucose using *Corynebacterium glutamicum* transgenic strains for 4-HBA-producing gene

| Strain | Host strain | Origin of 4-hydroxybenzoic acid-producing gene | Type of introduced mutation* | Amount of produced 4-hydroxybenzoic acid (mM) (After 24 hours) |
|---|---|---|---|---|
| HBA42 | *Corynebacterium glutamicum* R | *Providencia stuartii* | Wild type | 1.15 |
| HBA43 | | | V80A | 1.51 |
| HBA44 | | | V80C | 1.83 |
| HBA45 | | *Providencia rustigianii* | Wild type | 1.90 |
| HBA46 | | | V80A | 2.44 |
| HBA47 | | | V80C | 3.03 |
| HBA48 | | *Escherichia coli* | Wild type | 0.67 |
| HBA49 | | | I79A | 1.42 |
| HBA50 | | | I79C | 1.44 |
| HBA51 | | *Cronobacter sakazakii* | Wild type | 1.48 |
| HBA52 | | | I79A | 2.53 |
| HBA53 | | | I79C | 2.69 |

In the column of the "Type of introduced mutation*", A means "a mutation to alanine", and C means "a mutation to cysteine". Also, V means "a mutation of valine", and I means "a mutation of isoleucine". In addition, 80 means "position 80" and 79 means "position 79".

*Corynebacterium glutamicum* HBA-47 was deposited in Incorporated Administrative Agency National Institute of Technology and Evaluation, NITE Patent Microorganisms Depositary (2-5-8 Kazusakamatari, Kisarazu-shi, Chiba 292-0818 Japan) under Accession Number NITE BP-01849 on Apr. 25, 2014. The strain was deposited internationally under the Budapest Treaty and is available to the public under the conditions specified in 37 CFR 1.808. Similarly, *Corynebacterium glutamicum* R was deposited in Incorporated Administrative Agency National Institute of Technology and Evaluation, NITE Patent Microorganisms Depositary (2-5-8 Kazusakamatari, Kisarazu-shi, Chiba 292-0818 Japan) under Accession Number FERM BP-18976 on Aug. 20, 2002 and a request to convert the original deposit to a deposit under the Budapest Treaty was filed on Nov. 14, 2013. The strain was deposited internationally under the Budapest Treaty and is available to the public under the conditions specified in 37 CFR 1.808.

INDUSTRIAL APPLICABILITY

According to the present invention, using microorganisms, 4-HBA can be produced from glucose or the like with a practical efficiency.

---

The invention claimed is:

1. A transformant obtained by introducing into a coryneform bacterium host cell a DNA which encodes a mutant chorismate-pyruvate lyase, wherein the mutant chorismate-pyruvate lyase is a variant of the polypeptide of SEQ ID NO: 1, wherein said variant has at least 90% sequence identity with the polypeptide of SEQ ID NO: 1, 2, 3, 4, 5, 6, 7, 8 or 9, wherein said variant has chorismate-pyruvate lyase activity, and wherein said variant comprises an alanine, cysteine, threonine, serine, or asparagine at the position corresponding to position 80 of the polypeptide of SEQ ID NO: 1.

2. The transformant of claim 1, wherein the DNA is
(a) a DNA having 90% or more of identity with any one of SEQ ID NO: 10 to 16, wherein gtc at positions corresponding to positions 240 to 242 in a chorismate-pyruvate lyase gene of *Pantoea ananatis* consisting of the base sequence of SEQ ID NO: 10, a chorismate-pyruvate lyase gene of *Providencia stuartii* consisting of the base sequence of SEQ ID NO: 11, a chorismate-pyruvate lyase gene of *Providencia rustigianii* consisting of the base sequence of SEQ ID NO: 12, a chorismate-pyruvate lyase gene of *Providencia sneebia* consisting of the base sequence of SEQ ID NO: 13, a chorismate-pyruvate lyase gene of *Providencia rettgeri* consisting of the base sequence of SEQ ID NO: 14, a chorismate-pyruvate lyase gene of *Providencia alcalifaciens* consisting of the base sequence of SEQ ID NO: 15, or a chorismate-pyruvate lyase gene of *Providencia burhodogranariea* consisting of the base sequence of SEQ ID NO: 16 is replaced with a DNA segment which encodes a single amino acid selected from the group consisting of alanine, cysteine, threonine, serine, and asparagine,
(b) a DNA having 90% or more of identity with SEQ ID NO: 17, wherein atc at positions corresponding to positions 237 to 239 in a chorismate-pyruvate lyase gene of *Escherichia coli* consisting of the base sequence of SEQ ID NO: 17 is replaced with a DNA segment which encodes a single amino acid selected from the group consisting of alanine, cysteine, threonine, serine, and asparagine, or (c) a DNA having 90% or more of identity with SEQ ID NO: 18, wherein atc at positions corresponding to positions 237 to 239 in a chorismate-pyruvate lyase gene of *Cronobacter sakazakii* consisting of the base sequence of SEQ ID NO: 18 with a DNA segment which encodes a single amino acid that is different from isoleucine.

3. The transformant of claim 1, wherein the coryneform bacterium host cell is a *Corynebacterium glutamicum*.

4. The transformant of claim 3, wherein the *Corynebacterium glutamicum* is *Corynebacterium glutamicum* R deposited under Accession Number FERM BP-18976, ATCC13032, or ATCC13869.

5. A *Corynebacterium glutamicum* transformant, wherein said transformant is *Corynebacterium glutamicum* HBA-47 deposited at NITE under (Accession Number BP-01849.

6. A process for producing 4-hydroxybenzoic acid or a salt thereof, which comprises a step of culturing the transformant of claim 1 in a reaction mixture containing at least one starting compound selected from the group consisting of a sugar, a compound that can be metabolized into chorismic acid by the transformant, chorismic acid, and a salt thereof, and a step of recovering 4-hydroxybenzoic acid or a salt thereof from the reaction mixture.

7. The process of claim 6, wherein the transformant is cultured under aerobic conditions.

* * * * *

SEQUENCE LISTING

<160> NUMBER OF SEQ ID NOS: 44

<210> SEQ ID NO 1
<211> LENGTH: 170
<212> TYPE: PRT
<213> ORGANISM: Pantoea ananatis

<400> SEQUENCE: 1

```
Met Thr Gln Asp Pro Leu Arg Ser Leu Arg Ser Leu Asn Trp Leu Ala
1               5                   10                  15

Leu Asp Asp Ala Ala Leu Thr Gln Pro Leu Arg Asp Trp Leu Met Glu
            20                  25                  30

Glu Asp Ser Met Thr Arg Arg Phe Glu Gln His Cys Gln Lys Val Arg
        35                  40                  45

Val Glu Pro Val Arg Glu Asp Phe Ile Ser Ala Asp Glu Leu Gly Asp
    50                  55                  60

Glu Gly Ala Leu Leu Pro Ala Asp Gln Arg Phe Trp Leu Arg Glu Val
65                  70                  75                  80

Ile Leu Tyr Gly Asp Glu Glu Pro Trp Leu Ala Gly Arg Thr Leu Val
                85                  90                  95

Pro Glu Ser Thr Leu Asn Gly Pro Glu Ala Met Leu Gln Gln Leu Gly
            100                 105                 110

Thr Arg Pro Leu Gly Arg Tyr Leu Phe Ser Ser Ser Thr Leu Thr Arg
        115                 120                 125

Asp Phe Ile Glu Pro Gly Arg Val Asp Ala Leu Trp Gly Arg Arg Ser
    130                 135                 140

Arg Leu Arg Leu Ser Gly Lys Pro Leu Leu Leu Thr Glu Leu Phe Leu
145                 150                 155                 160

Pro Ala Ser Pro Leu Tyr Arg Asp Gln Gly
                165                 170
```

<210> SEQ ID NO 2
<211> LENGTH: 168
<212> TYPE: PRT
<213> ORGANISM: Providencia stuartii

<400> SEQUENCE: 2

```
Met Asp Glu Thr Leu Phe Ile Ser His Pro Ile Thr Trp Leu Ser Glu
1               5                   10                  15

Asp Asp Asp Leu Val Pro Glu Asn Val Leu Asp Trp Leu His Glu Leu
            20                  25                  30

Gly Ser Met Thr Lys Arg Leu Glu Gln His Cys Gln Arg Val Thr Val
        35                  40                  45

Val Pro Tyr Thr Gln Arg Tyr Val Thr Gln Glu Ala Leu Ser Glu Glu
    50                  55                  60

Glu Ala Ala Cys Leu Pro Val Ser Glu Tyr Tyr Trp Leu Arg Glu Val
65                  70                  75                  80

Ile Met Tyr Gly Asp Asn Ile Pro Trp Leu Leu Gly Arg Thr Leu Ile
                85                  90                  95

Pro Gln Glu Thr Leu Thr Gly Gly Asp Arg Lys Leu Ile Asp Ile Gly
            100                 105                 110
```

```
Ala Val Pro Leu Gly Arg Tyr Leu Phe Ser His Asp Asn Leu Ser Arg
            115                 120                 125

Asp Tyr Ile His Ile Gly Gln Gln Asn Leu Arg Trp Ile Arg Arg Ser
        130                 135                 140

Leu Leu Arg Leu Ser Glu Lys Pro Leu Leu Leu Thr Glu Leu Phe Leu
145                 150                 155                 160

Pro Glu Ser Pro Ala Tyr Lys Arg
                165
```

<210> SEQ ID NO 3
<211> LENGTH: 167
<212> TYPE: PRT
<213> ORGANISM: Providencia rustigianii

<400> SEQUENCE: 3

```
Met His Glu Thr Ile Phe Thr His His Pro Ile Asp Trp Leu Asn Glu
1               5                   10                  15

Asp Asp Glu Ser Val Pro Asn Ser Val Leu Asp Trp Leu Gln Glu Arg
            20                  25                  30

Gly Ser Met Thr Lys Arg Phe Glu Gln His Cys Gln Lys Val Thr Val
        35                  40                  45

Ile Pro Tyr Leu Glu Arg Tyr Ile Thr Pro Glu Met Leu Ser Ala Asp
    50                  55                  60

Glu Ala Glu Arg Leu Pro Glu Ser Gln Arg Tyr Trp Leu Arg Glu Val
65                  70                  75                  80

Ile Met Tyr Gly Asp Asn Ile Pro Trp Leu Ile Gly Arg Thr Leu Ile
                85                  90                  95

Pro Glu Glu Thr Leu Thr Asn Asp Lys Lys Leu Val Asp Ile Gly
            100                 105                 110

Arg Val Pro Leu Gly Arg Tyr Leu Phe Ser His Asp Ser Leu Thr Arg
            115                 120                 125

Asp Tyr Ile Asp Ile Gly Thr Ser Ala Asp Arg Trp Val Arg Arg Ser
        130                 135                 140

Leu Leu Arg Leu Ser Gln Lys Pro Leu Leu Leu Thr Glu Ile Phe Leu
145                 150                 155                 160

Pro Glu Ser Pro Ala Tyr Arg
                165
```

<210> SEQ ID NO 4
<211> LENGTH: 168
<212> TYPE: PRT
<213> ORGANISM: Providencia sneebia

<400> SEQUENCE: 4

```
Met Asp Asp Thr Leu Phe Thr Ser His Pro Ile Thr Trp Leu Ser Glu
1               5                   10                  15

Thr Asp Asn Val Ile Pro Glu Asn Met Leu Ser Trp Leu Gln Glu Leu
            20                  25                  30

Gly Ser Met Thr Lys Arg Leu Glu Gln Tyr Cys Gln Ser Leu Thr Val
        35                  40                  45

Thr Pro Tyr Val Gln Lys Tyr Val Ser Arg Asn Met Leu Ser Asp Asp
    50                  55                  60

Glu Ala Gln Cys Leu Pro Glu Ser Ser Tyr Trp Leu Arg Glu Val
65                  70                  75                  80

Ile Ile Tyr Gly Asp Asn Ile Pro Trp Leu Leu Gly Arg Thr Leu Ile
                85                  90                  95
```

```
Pro Gln Glu Thr Leu Ser Gly Asp Asp Gln Arg Ile Val Asp Ile Gly
                100                 105                 110

Thr Leu Pro Leu Gly Arg Tyr Leu Phe Ser His Asp Asn Leu Thr Arg
            115                 120                 125

Asp Tyr Ile His Ile Gly Gln Gln Glu Gln Arg Trp Leu Arg Arg Ser
        130                 135                 140

Arg Leu Arg Leu Ser Asn Asn Pro Leu Leu Leu Thr Glu Leu Phe Leu
145                 150                 155                 160

Pro Glu Ser Pro Ala Tyr Lys Arg
                165

<210> SEQ ID NO 5
<211> LENGTH: 167
<212> TYPE: PRT
<213> ORGANISM: Providencia rettgeri

<400> SEQUENCE: 5

Met Asp Glu Thr Leu Phe Thr Ser Gln Pro Ile His Trp Leu Ala Glu
1               5                   10                  15

Asn Asp Lys Ile Val Pro Ala Asn Val Leu Asp Trp Leu Leu Glu Leu
            20                  25                  30

Gly Ser Met Thr Lys Arg Phe Glu Gln His Ser Gln Gln Val Thr Val
        35                  40                  45

Ile Pro Tyr Leu Glu Arg Tyr Ile Thr Gln Asp Lys Leu Ser Ala Asp
    50                  55                  60

Glu Met Leu Ser Leu Pro Glu Ser Gln Arg Tyr Trp Val Arg Glu Val
65                  70                  75                  80

Val Met Tyr Gly Asp Gly Ile Pro Trp Leu Leu Gly Arg Thr Ile Ile
                85                  90                  95

Pro Glu Glu Thr Leu Thr Asp Asp Gln Gln Leu Val Asp Ile Gly
                100                 105                 110

Arg Met Pro Leu Gly Arg Tyr Leu Phe Ser Arg Asp Ser Leu Thr Arg
            115                 120                 125

Asp Tyr Ile His Ile Gly Ser Cys Ala Asn Arg Trp Val Arg Cys Ser
        130                 135                 140

Arg Leu Arg Leu Ser Asp Lys Pro Leu Leu Leu Thr Glu Ile Phe Leu
145                 150                 155                 160

Pro Glu Ser Pro Ala Tyr Arg
                165

<210> SEQ ID NO 6
<211> LENGTH: 167
<212> TYPE: PRT
<213> ORGANISM: Providencia alcalifaciens

<400> SEQUENCE: 6

Met His Glu Thr Ile Phe Thr Ser His Pro Ile Ser Trp Phe Val Glu
1               5                   10                  15

Gly Glu Glu Ser Val Pro Glu Asn Val Leu Gly Trp Leu Gln Glu Gln
            20                  25                  30

Arg Ser Met Thr Lys Arg Phe Glu Gln His Cys Gln Lys Val Thr Val
        35                  40                  45

Ile Pro Tyr Leu Glu Arg Tyr Ile Ser Leu Asp Met Leu Thr Thr Asp
    50                  55                  60

Glu Gln Lys Cys Leu Pro Ile Ser Glu Arg Tyr Trp Leu Arg Glu Val
65                  70                  75                  80
```

```
Ile Met Tyr Gly Asp Asn Ile Pro Trp Leu Ile Gly Arg Thr Leu Ile
                85                  90                  95

Pro Glu Glu Thr Leu Thr Asp Asn Asp Lys Lys Leu Val Glu Leu Gly
            100                 105                 110

Arg Val Pro Leu Gly Arg Tyr Leu Phe Ser His Glu His Leu Thr Arg
            115                 120                 125

Asp Tyr Ile Glu Met Gly Thr Ser Ala Asp Arg Trp Val Arg Arg Ser
            130                 135                 140

Leu Leu Arg Leu Ser Gln Lys Pro Leu Leu Leu Thr Glu Ile Phe Leu
145                 150                 155                 160

Pro Glu Ser Pro Ala Tyr Arg
                165
```

<210> SEQ ID NO 7
<211> LENGTH: 168
<212> TYPE: PRT
<213> ORGANISM: Providencia burhodogranariea

<400> SEQUENCE: 7

```
Met Asp Glu Thr Leu Phe Thr Ser His Pro Ile Thr Trp Leu Pro Glu
1               5                   10                  15

Ala Asp Asp Leu Val Pro Asp Asn Ile Leu Asp Trp Leu His Glu Leu
            20                  25                  30

Gly Ser Met Thr Lys Arg Leu Glu Gln His Cys Gln Cys Val Thr Val
        35                  40                  45

Ile Pro Cys Ala Gln Arg Tyr Val Thr Lys Glu Ala Leu Ser Asp Asp
    50                  55                  60

Glu Thr Gln Cys Leu Pro Val Ser Glu Tyr Tyr Trp Leu Arg Glu Val
65                  70                  75                  80

Ile Met Tyr Gly Asp Asn Ile Pro Trp Leu Leu Gly Arg Thr Leu Ile
                85                  90                  95

Pro Gln Glu Thr Leu Thr Gly Glu Asp Gln Lys Leu Ile Asp Ile Gly
            100                 105                 110

Ala Val Pro Leu Gly Arg Tyr Leu Phe Ser His Asp Asn Leu Thr Arg
            115                 120                 125

Asp Tyr Ile His Ile Gly Gln Gln Asn Ser Arg Trp Leu Arg Arg Ser
            130                 135                 140

Arg Leu Arg Leu Ser Asn Lys Pro Leu Leu Leu Thr Glu Leu Phe Leu
145                 150                 155                 160

Pro Glu Ser Pro Ala Tyr Lys Arg
                165
```

<210> SEQ ID NO 8
<211> LENGTH: 165
<212> TYPE: PRT
<213> ORGANISM: Escherichia coli

<400> SEQUENCE: 8

```
Met Ser His Pro Ala Leu Thr Gln Leu Arg Ala Leu Arg Tyr Cys Lys
1               5                   10                  15

Glu Ile Pro Ala Leu Asp Pro Gln Leu Leu Asp Trp Leu Leu Leu Glu
            20                  25                  30

Asp Ser Met Thr Lys Arg Phe Glu Gln Gln Gly Lys Thr Val Ser Val
        35                  40                  45

Thr Met Ile Arg Glu Gly Phe Val Glu Gln Asn Glu Ile Pro Glu Glu
    50                  55                  60
```

```
Leu Pro Leu Leu Pro Lys Glu Ser Arg Tyr Trp Leu Arg Glu Ile Leu
 65                  70                  75                  80

Leu Cys Ala Asp Gly Glu Pro Trp Leu Ala Gly Arg Thr Val Val Pro
                 85                  90                  95

Val Ser Thr Leu Ser Gly Pro Glu Leu Ala Leu Gln Lys Leu Gly Lys
            100                 105                 110

Thr Pro Leu Gly Arg Tyr Leu Phe Thr Ser Ser Thr Leu Thr Arg Asp
        115                 120                 125

Phe Ile Glu Ile Gly Arg Asp Ala Gly Leu Trp Gly Arg Ser Arg
    130                 135                 140

Leu Arg Leu Ser Gly Lys Pro Leu Leu Leu Thr Glu Leu Phe Leu Pro
145                 150                 155                 160

Ala Ser Pro Leu Tyr
                165

<210> SEQ ID NO 9
<211> LENGTH: 169
<212> TYPE: PRT
<213> ORGANISM: Cronobacter sakazakii

<400> SEQUENCE: 9

Met Ser His Pro Ala Leu Arg Gln Leu Arg Ala Leu Ser Phe Phe Asp
 1               5                  10                  15

Asp Ile Ser Thr Leu Asp Ser Ser Leu Leu Asp Trp Leu Met Leu Glu
                20                  25                  30

Asp Ser Met Thr Arg Arg Phe Glu Gly Phe Cys Glu Arg Val Thr Val
            35                  40                  45

Asp Met Leu Phe Glu Gly Phe Val Gly Pro Glu Ala Leu Glu Glu Glu
        50                  55                  60

Gly Glu Phe Leu Pro Asp Glu Pro Arg Tyr Trp Leu Arg Glu Ile Leu
 65                  70                  75                  80

Leu Cys Gly Asp Gly Val Pro Trp Leu Val Gly Arg Thr Leu Val Pro
                 85                  90                  95

Glu Ser Thr Leu Cys Gly Pro Glu Leu Ala Leu Gln Gln Leu Gly Thr
            100                 105                 110

Thr Pro Leu Gly Arg Tyr Leu Phe Thr Ser Ser Thr Leu Thr Arg Asp
        115                 120                 125

Phe Ile Gln Pro Gly Arg Ser Asp Glu Leu Trp Gly Arg Arg Ser Leu
    130                 135                 140

Leu Arg Leu Ser Gly Lys Pro Leu Leu Leu Thr Glu Leu Phe Leu Pro
145                 150                 155                 160

Ala Ser Pro Leu Tyr Gly Glu Glu Lys
                165

<210> SEQ ID NO 10
<211> LENGTH: 513
<212> TYPE: DNA
<213> ORGANISM: Pantoea ananatis

<400> SEQUENCE: 10
atgacgcaag acccgctccg ttcgttacgt tcacttaact ggctggcgct ggacgatgcc      60
gcattgacgc aaccgcttcg tgactggcta atggaagagg attccatgac gcgacgcttt     120
gaacagcatt gccagaaggt cagggtggaa cctgtacgtg aggactttat ctccgccgat     180
gaactcggcg atgaagggc attactccct gccgatcagc gtttctggct gcagaaagtc     240
attctctacg gggatgagga accttggctg gcagggcgca cgctggtgcc agaaagtacc     300
```

```
ctcaacggcc cggaagcgat gttacagcaa ctcggtacgc gcccgctggg gcgttatctg    360
ttctcgtcat caacgctgac ccgcgatttc attgagcctg gccgcgttga tgcgctctgg    420
ggacgccgct cgcgcctgcg actgtcaggg aaaccgctgc tgttaacgga actgttttta    480
ccggcttcgc cgctctatcg tgatcaaggt taa                                  513
```

<210> SEQ ID NO 11
<211> LENGTH: 507
<212> TYPE: DNA
<213> ORGANISM: Providencia stuartii

<400> SEQUENCE: 11

```
atggatgaaa cgcttttat ctctcacccg ataacatggc tatcagaaga tgatgacctt    60
gttcctgaaa atgttttaga ttggctacat gaactagggt cgatgacaaa acgcttagag    120
cagcattgcc aacgtgtcac ggttgttcct tatacgcaac gttatgtgac tcaagaggca    180
ttgagcgaag aagaagcggc gtgtttacct gtcagtgaat attattggtt acgtgaagtc    240
attatgtatg gtgataatat tccatggtta cttggacgaa cgttaattcc acaggagaca    300
ttgactggtg aagaccggaa acttattgat atcggtgctg taccgttagg cgttatctc    360 tttagccatg ataatctttc ccgtgattat attcatatag ggcagcaaaa tttgcgatgg    420
atccgccgct ctctattaag attatctgaa aaacctttat tattaaccga actgttttta    480
cctgaatcac ctgcatataa aagataa                                        507
```

<210> SEQ ID NO 12
<211> LENGTH: 504
<212> TYPE: DNA
<213> ORGANISM: Providencia rustigianii

<400> SEQUENCE: 12

```
atgcatgaaa caattttac ccatcatccc attgattggc taaacgagga tgatgagtca     60
gttcctaaca gtgtactaga ttggctgcaa gagcgtggtt caatgactaa acggttcgag    120
cagcattgcc aaaaagtcac ggtaattccc tatttagagc gctatatcac tccagagatg    180
ctgagcgctg atgaagccga gcgtttaccc gaaagtcaac gttactggtt gcagaaagtc    240
attatgtatg gggataatat tccgtggttg ataggcagaa cattgatccc tgaagagacc    300
ctcaccaacg atgataaaaa gctggtggac attggtcgtg tgccattagg cgttaccttt    360
tttagtcatg atagtcttac ccgagattat attgatattg caccagtgc ggatcgttgg    420 gtgcgacgtt ctctgctgag attatctcaa agcccttat tattaactga aatatttta     480 cctgaatcac ctgcatatag ataa                                           504
```

<210> SEQ ID NO 13
<211> LENGTH: 507
<212> TYPE: DNA
<213> ORGANISM: Providencia sneebia

<400> SEQUENCE: 13

```
atggatgata cgctttttac ctctcacccg ataacatggt tatcagagac tgataatgtt     60
attcctgaaa atatgttaag ttggttacaa gaactcgggt caatgacaaa agcttagaa    120 caatattgcc agtctttgac tgtcaccccct tatgtgcaaa atatgtttc cagaaacatg    180 ctgagtgatg atgaagctca atgtttacct gaaagctcaa gttattggct aagagaagtg    240
attatctatg gggataatat cccttggttg ctagggcgaa cgctaattcc gcaagaaaca    300
```

```
ttgagtggcg atgaccaaag aattgtcgat attggtacgc tgcctttagg ccgttatcta    360
tttagtcatg ataatctgac tcgtgattat attcatattg ggcaacagga gcagcgatgg    420
ctgcgtcgtt cgcgattaag gctatcgaat aatccttat tattaactga attgttttta    480
cctgaatcac ctgcatataa aagataa                                        507
```

```
<210> SEQ ID NO 14
<211> LENGTH: 504
<212> TYPE: DNA
<213> ORGANISM: Providencia rettgeri

<400> SEQUENCE: 14
atggatgaaa cgcttttttac ttctcagccg attcactggc tggcggagaa cgataaaata   60
gtgcctgcca atgtattaga ttggctatta gagctcggct ccatgacaaa cgttttgag    120 cagcatagcc agcaagttac cgtgatacct tatttagagc gctatataac acaagataag   180
ctgagtgcag atgaaatgct gtcttttacct gaaagccaac gttattgggt cagagaagtt   240
gtcatgtatg gagatggtat cccttggtta ctgggccgaa cgataatccc tgaagaaaca   300
ctgactgatg atgaccagca actggtagat attgggagaa tgccgttagg gcgttatta    360 tttagccgtg acagcttaac tcgagattat attcatattg gttcttgcgc aaaccgttgg   420
gtacgttgtt ctcggttaag attatcggat aaacccttac tattaacaga atatttta    480 cctgaatcac ctgcatatcg ttaa                                          504
```

```
<210> SEQ ID NO 15
<211> LENGTH: 504
<212> TYPE: DNA
<213> ORGANISM: Providencia alcalifaciens

<400> SEQUENCE: 15
atgcatgaaa cgatttttac ctctcatcct ataagttggt tcgtagaagg cgaagagagt   60
gttcctgaaa atgtattagg ttggttgcaa gagcaaaggt cgatgaccaa acggtttgag   120
cagcattgtc agaaagtgac ggtgatacct tatttagaac gctatatctc actggatatg   180
ctcaccaccg acgaacaaaa atgcttacca attagtgagc gttattggct acgggaagtg   240
attatgtatg gggataatat cccttggttg attggcagaa cgctgatccc agaagagacg   300
ctcaccgata tgacaaaaa attagtcgag cttgggcgag tcccattagg gcgctatctc    360
tttagtcatg aacacctaac ccgagattat attgaaatgg gcaccagtgc tgaccgctgg   420
gttcgccgtt ccttacttag actgtcccaa aaaccattat tattaaccga atatttta    480 cctgaatcac ctgcatatag ataa                                          504
```

```
<210> SEQ ID NO 16
<211> LENGTH: 507
<212> TYPE: DNA
<213> ORGANISM: Providencia burhodogranariea

<400> SEQUENCE: 16
atggatgaaa cgcttttttac ctctcacccg ataacgtggc taccagaggc cgatgacctt   60
gttcctgata atatttaga ctggttgcat gagcttgggt caatgacaaa cgtttagag   120 cagcactgcc agtgtgttac cgttatccct tgtgcgcagc gatatgtgac taagaagct    180 ctcagtgatg atgaaactca atgtttaccg gtgagtgagt actattggtt acgggaggtt   240
attatgtatg gtgataatat tccctggtta ctcggccgaa cactaattcc gcaagaaaca   300
ttgaccggtg aagaccaaaa gctcattgat attggtgctg taccattagg gcgttatcta   360
```

```
tttagtcatg ataatcttac ccgggattat attcatatag ggcagcaaaa ttctcgatgg    420
ctccgtcgct ctcgattaag gttatcaaac aaaccgttat tattaactga attattttta    480
cctgaatcac ctgcttataa aagataa                                        507
```

<210> SEQ ID NO 17
<211> LENGTH: 498
<212> TYPE: DNA
<213> ORGANISM: Escherichia coli

<400> SEQUENCE: 17

```
atgtcacacc ccgcgttaac gcaactgcgt gcgctgcgct attgtaaaga gatccctgcc     60
ctggatccgc aactgctcga ctggctgttg ctggaggatt ccatgacaaa acgttttgaa    120
cagcagggaa aaacggtaag cgtgacgatg atccgcgaag ggtttgtcga gcagaatgaa    180
atccccgaag aactgccgct gctgccgaaa gagtctcgtt actggttacg tgaaattttg    240
ttatgtgccg atggtgaacc gtggcttgcc ggtcgtaccg tcgttcctgt gtcaacgtta    300
agcgggccgg agctggcgtt acaaaaattg ggtaaaacgc cgttaggacg ctatctgttc    360
acatcatcga cattaacccg ggactttatt gagataggcc gtgatgccgg gctgtggggg    420
cgacgttccc gcctgcgatt aagcggtaaa ccgctgttgc taacagaact gttttttaccg    480 gcgtcaccgt tgtactaa                                                  498
```

<210> SEQ ID NO 18
<211> LENGTH: 510
<212> TYPE: DNA
<213> ORGANISM: Cronobacter sakazakii

<400> SEQUENCE: 18

```
atgtcccatc ccgcgctgag acaactgcgc gcgttgtcct ttttgacga tatcagcacg      60 cttgatagtt cgctgctcga ctggctgatg ctggaagatt ccatgacccg ccgtttcgaa    120
ggcttttgcg agcgcgtgac ggtcgacatg ctgtttgagg gctttgtcgg ccccgaggcg    180
ctggaggaag agggcgagtt tttgcctgat gagccgcgct actggctgcg cgaaatcctg    240
ctgtgcggcg acgcgtgcc gtggctggtt gggcgcacgc tggtgccgga gtctacactt    300
tgtgggccgg agctggcgtt gcagcagctc ggtaccacgc cgctgggccg ttatctgttt    360
acctcatcca ccctcacgcg tgattttatc cagccgggcc gcagcgacga actctgggga    420
cgccgctctc tgctgaggct ttccggcaaa ccgctgctgc tgactgaact gttttttacct    480 gcatcaccct tgtacggaga ggaaaaataa                                    510
```

<210> SEQ ID NO 19
<211> LENGTH: 24
<212> TYPE: DNA
<213> ORGANISM: Artificial sequence
<220> FEATURE:
<223> OTHER INFORMATION: PCR primer

<400> SEQUENCE: 19

```
ctctcatatg acgcaagacc cgct                                           24
```

<210> SEQ ID NO 20
<211> LENGTH: 33
<212> TYPE: DNA
<213> ORGANISM: Artificial sequence
<220> FEATURE:
<223> OTHER INFORMATION: PCR primer

<400> SEQUENCE: 20
ctctcatatg ttaaccttga tcacgataga gcg                                    33

<210> SEQ ID NO 21
<211> LENGTH: 25
<212> TYPE: DNA
<213> ORGANISM: Artificial sequence
<220> FEATURE:
<223> OTHER INFORMATION: PCR primer

<400> SEQUENCE: 21
cgagaagcaa ttctctacgg ggatg                                             25

<210> SEQ ID NO 22
<211> LENGTH: 19
<212> TYPE: DNA
<213> ORGANISM: Artificial sequence
<220> FEATURE:
<223> OTHER INFORMATION: PCR primer

<400> SEQUENCE: 22
cagccagaaa cgctgatcg                                                    19

<210> SEQ ID NO 23
<211> LENGTH: 22
<212> TYPE: DNA
<213> ORGANISM: Artificial sequence
<220> FEATURE:
<223> OTHER INFORMATION: PCR primer

<400> SEQUENCE: 23
tgcattctct acggggatga gg                                                22

<210> SEQ ID NO 24
<211> LENGTH: 21
<212> TYPE: DNA
<213> ORGANISM: Artificial sequence
<220> FEATURE:
<223> OTHER INFORMATION: PCR primer

<400> SEQUENCE: 24
ttctcgcagc cagaaacgct g                                                 21

<210> SEQ ID NO 25
<211> LENGTH: 34
<212> TYPE: DNA
<213> ORGANISM: Artificial sequence
<220> FEATURE:
<223> OTHER INFORMATION: PCR primer

<400> SEQUENCE: 25
ctctcatatg gatgaaacgc tttttatctc tcac                                   34

<210> SEQ ID NO 26
<211> LENGTH: 30
<212> TYPE: DNA
<213> ORGANISM: Artificial sequence
<220> FEATURE:
<223> OTHER INFORMATION: PCR primer

<400> SEQUENCE: 26
ctctcatatg tccctccatt tgttgtgctc                                        30

<210> SEQ ID NO 27
<211> LENGTH: 36

```
<212> TYPE: DNA
<213> ORGANISM: Artificial sequence
<220> FEATURE:
<223> OTHER INFORMATION: PCR primer

<400> SEQUENCE: 27
ctctcatatg catgaaacaa tttttaccca tcatcc                              36

<210> SEQ ID NO 28
<211> LENGTH: 42
<212> TYPE: DNA
<213> ORGANISM: Artificial sequence
<220> FEATURE:
<223> OTHER INFORMATION: PCR primer

<400> SEQUENCE: 28
ctctcatatg gattatgtta gatagttatc tatatgcagg tg                       42

<210> SEQ ID NO 29
<211> LENGTH: 26
<212> TYPE: DNA
<213> ORGANISM: Artificial sequence
<220> FEATURE:
<223> OTHER INFORMATION: PCR primer

<400> SEQUENCE: 29
ctctcatatg tcacaccccg cgttaa                                         26

<210> SEQ ID NO 30
<211> LENGTH: 29
<212> TYPE: DNA
<213> ORGANISM: Artificial sequence
<220> FEATURE:
<223> OTHER INFORMATION: PCR primer

<400> SEQUENCE: 30
ctctcatatg ttagtacaac ggtgacgcc                                      29

<210> SEQ ID NO 31
<211> LENGTH: 27
<212> TYPE: DNA
<213> ORGANISM: Artificial sequence
<220> FEATURE:
<223> OTHER INFORMATION: PCR primer

<400> SEQUENCE: 31
ctctcatatg tcccatcccg cgctgag                                        27

<210> SEQ ID NO 32
<211> LENGTH: 30
<212> TYPE: DNA
<213> ORGANISM: Artificial sequence
<220> FEATURE:
<223> OTHER INFORMATION: PCR primer

<400> SEQUENCE: 32
ctctcatatg tattctgcgt caggctccac                                     30

<210> SEQ ID NO 33
<211> LENGTH: 37
<212> TYPE: DNA
<213> ORGANISM: Artificial sequence
<220> FEATURE:
<223> OTHER INFORMATION: PCR primer

<400> SEQUENCE: 33
```

```
gcaattatgt atggtgataa tattccatgg ttacttg                              37

<210> SEQ ID NO 34
<211> LENGTH: 37
<212> TYPE: DNA
<213> ORGANISM: Artificial sequence
<220> FEATURE:
<223> OTHER INFORMATION: PCR primer

<400> SEQUENCE: 34
tgcattatgt atggtgataa tattccatgg ttacttg                              37

<210> SEQ ID NO 35
<211> LENGTH: 29
<212> TYPE: DNA
<213> ORGANISM: Artificial sequence
<220> FEATURE:
<223> OTHER INFORMATION: PCR primer

<400> SEQUENCE: 35
ttcacgtaac caataatatt cactgacag                                       29

<210> SEQ ID NO 36
<211> LENGTH: 27
<212> TYPE: DNA
<213> ORGANISM: Artificial sequence
<220> FEATURE:
<223> OTHER INFORMATION: PCR primer

<400> SEQUENCE: 36
attatgtatg gggataatat tccgtgg                                         27

<210> SEQ ID NO 37
<211> LENGTH: 24
<212> TYPE: DNA
<213> ORGANISM: Artificial sequence
<220> FEATURE:
<223> OTHER INFORMATION: PCR primer

<400> SEQUENCE: 37
gcattctcgc aaccagtaac gttg                                            24

<210> SEQ ID NO 38
<211> LENGTH: 24
<212> TYPE: DNA
<213> ORGANISM: Artificial sequence
<220> FEATURE:
<223> OTHER INFORMATION: PCR primer

<400> SEQUENCE: 38
tgcttctcgc aaccagtaac gttg                                            24

<210> SEQ ID NO 39
<211> LENGTH: 25
<212> TYPE: DNA
<213> ORGANISM: Artificial sequence
<220> FEATURE:
<223> OTHER INFORMATION: PCR primer

<400> SEQUENCE: 39
gcattgttat gtgccgatgg tgaac                                           25

<210> SEQ ID NO 40
<211> LENGTH: 25
<212> TYPE: DNA
<213> ORGANISM: Artificial sequence
```

```
<220> FEATURE:
<223> OTHER INFORMATION: PCR primer

<400> SEQUENCE: 40
tgcttgttat gtgccgatgg tgaac                                        25

<210> SEQ ID NO 41
<211> LENGTH: 22
<212> TYPE: DNA
<213> ORGANISM: Artificial sequence
<220> FEATURE:
<223> OTHER INFORMATION: PCR primer

<400> SEQUENCE: 41
ttcacgtaac cagtaacgag ac                                           22

<210> SEQ ID NO 42
<211> LENGTH: 19
<212> TYPE: DNA
<213> ORGANISM: Artificial sequence
<220> FEATURE:
<223> OTHER INFORMATION: PCR primer

<400> SEQUENCE: 42
gcactgctgt gcggcgacg                                               19

<210> SEQ ID NO 43
<211> LENGTH: 19
<212> TYPE: DNA
<213> ORGANISM: Artificial sequence
<220> FEATURE:
<223> OTHER INFORMATION: PCR primer

<400> SEQUENCE: 43
tgcctgctgt gcggcgacg                                               19

<210> SEQ ID NO 44
<211> LENGTH: 18
<212> TYPE: DNA
<213> ORGANISM: Artificial sequence
<220> FEATURE:
<223> OTHER INFORMATION: PCR primer

<400> SEQUENCE: 44
ttcgcgcagc cagtagcg                                                18
```